United States Patent [19]

Harnisch et al.

[11] 3,950,347
[45] Apr. 13, 1976

[54] NAPHTHOLACTAM DYESTUFFS

[75] Inventors: Horst Harnisch, Cologne; Alfred Brack, Odenthal, both of Germany

[73] Assignee: Bayer Aktiengesellschaft, Leverkusen, Germany

[22] Filed: May 25, 1973

[21] Appl. No.: 363,989

[30] Foreign Application Priority Data

May 26, 1972 Germany............................ 2225648

[52] U.S. Cl. .... 260/294.8 B; 260/249.5; 260/270 B; 260/270 H; 260/294.8 R; 260/294.9; 260/295 T; 260/308 B; 8/1 B
[51] Int. Cl.²...................................... C07D 213/71
[58] Field of Search ...... 260/308 B, 294.9, 294.8 B, 260/295 T

[56] References Cited
UNITED STATES PATENTS 2,647,112 7/1953 Glenz et al...................... 260/308 B
3,304,311 2/1967 Weber et al..................... 260/308 B Primary Examiner—Alan L. Rotman
Attorney, Agent, or Firm—Plumley & Tyner

[57] ABSTRACT

Naphtholactam dyestuffs of the formula

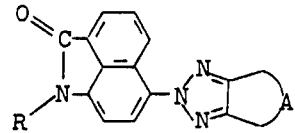

wherein A represents the remaining members of an aromatic ring system and R represents hydrogen, alkyl, aralkyl, cycloalkyl, alkyl, aryl or an alkylene radical bonded to the naphthalene ring in the 2-position, as well as thier preparation and their use for dyeing and printing natural and synthetic materials.

8 Claims, No Drawings

NAPHTHOLACTAM DYESTUFFS

The subject of the present invention are naphtholactam compounds of the general formula

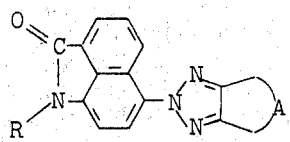

wherein
A represents the remaining members of an aromatic ring system and
R represents hydrogen, alkyl, aralkyl, cycloalkyl, aryl or an alkylene radical bonded to the naphthalene ring in the 2-position, as well as processes for their manufacture, and their use for dyeing, printing and bulk-dyeing of natural and synthetic materials, and the materials dyed and printed with these compounds.

Possible aromatic ring systems of which the remaining members are designated A are both monocyclic and condensed systems which can be built up of aromatic-carbocyclic and/or aromatic-heterocyclic rings fused in any desired manner and which optionally also contain fused partly saturated rings. Five-membered and six-membered rings are preferred.

As examples of such aromatic radicals there may be mentioned: the radicals of benzene, naphthalene, acenaphthene, tetralin, anthracene, phenanthrene, pyrene, pyridine, pyrimidine, pyrazole, indazole, benztriazole, benz[c,d]-indole, benzdioxane-(1,3), benzdioxane-(1,4), benzdioxole and coumarine.

The aromatic radicals A and the naphtholactam ring system can also carry substituents.

As examples of substituents on the naphtholactam ring system there may be mentioned alkyl, hydroxyl, alkoxy, halogen, nitro, amino, sulpho and sulphonamide groups; by alkyl groups there are especially to be understood those with 1-4 C atoms such as methyl, ethyl, isopropyl and n-butyl, by alkoxy groups there are especially to be understood those with 1-4 C atoms such as methoxy, ethoxy, n-propoxy, n-butoxy and isopropoxy, by halogen radicals there are to be understood, in addition to fluorine, especially chlorine and bromine and by sulphonamide groups there are especially to be understood sulphonamide radicals substituted by low molecular alkyl radicals such as methyl, ethyl and n-butyl.

Examples of possible substituents on aromatic rings of which the remaining members are designated A are: alkyl, alkoxy, halogen, amino, alkylamino, dialkylamino, acylamino, alkylacylamino, aryl, carboxyl, carboxylic acid ester, carboxylic acid amide and sulphonic acid amide, nitrile, sulpho and sulphinic acid groups, sulphonic acid amidines, alkylsulphonyl radicals and heterocyclic radicals.

By alkyl groups there are especially understood those with 1-4 C atoms such as methyl, ethyl, n-propyl, isopropyl and n-butyl radicals as well as trifluoromethyl groups.

Suitable alkoxy radicals preferably contain 1-12 C atoms and their C-chain can also be interrupted by oxygen bonded in the manner of an ether. As examples of such alkoxy radicals there may be mentioned: methoxy, carboxymethoxy, ethoxy, β-methoxyethoxy, β-ethoxy-ethoxy, β-carboxyethoxy, isopropoxy, n- or sec.-butoxy, i-amyloxy, n-octyloxy and n- dodecyloxy.

As halogen radicals there may be mentioned, in addition to fluorine, especially chlorine and bromine.

Alkylamino and dialkylamino radicals preferably contain alkyl groups with 1-4 C atoms which can be substituted by halogen, nitrile, hydroxyl or $C_1$-$C_4$-alkoxy or can together form a saturated heterocyclic five-membered or six-membered ring such as morpholine, N-($C_1$-$C_4$)-alkylpiperazine, piperidine or pyrrolidine.

Examples of alkyl and dialkylamino groups are methylamino, dimethylamino, ethylamino, diethylamino, n-butylamino, di-n-butylamino, di-β-cyanoethylamino, di-β-hydroxyethylamino, di-β-methoxyethylamino, di-β-chloroethylamino, β-bromoethylamino, and γ-hydroxy-n-propylamino radicals.

Examples of suitable acylamino groups are: alkylcarbonylamino groups with 1-6 C atoms which can also be substituted, for example by halogen or nitrile, such as acetylamino, trifluoroacetylamino, cyanoacetylamino, propionylamino, β-chloro-propionylamino, n-butyroylamino and n-caproylamino; aralkylcarbonylamino groups, especially phenylalkyl carbonylamino groups with 1-3 C atoms in the alkyl radical which are optionally substituted by halogen or $C_1$-$C_4$-alkyl, such as benzylcarbonylamino, p-chlorobenzylcarbonylamino, p-methylbenzylcarbonylamino, p-t-butylbenzylcarbonylamino, β-phenylethylcarbonylamino and γ-phenyl-n-propylcarbonylamino; arylcarbonylamino groups such as benzoylamino and naphthoylamino radicals which can be substituted by halogen, $C_1$-$C_4$-alkyl, $C_1$-$C_4$-alkoxy, nitrile and carboxylic acid alkyl ester with 1-4 C atoms in the alkyl radical, such as benzoylamino, p-methylbenzoylamino, p-ethoxybenzoylamino, p-cyanobenzoylamino, p-methoxycarbonylbenzoylamino, p-chlorobenzoylamino and m-bromobenzoylamino; alkylaminocarbonylamino and dialkylaminocarbonylamino radicals with 1-4 C atoms in the particular alkyl radical, such as methylamino-carbonylamino, ethylamino-carbonylzmino, diethylamino-carbonylamino and n-butylaminocarbonylamino; arylaminocarbonylamino radicals such as phenylamino-carbonylamino radicals which are optionally substituted by $C_1$-$C_4$-alkyl, halogen or $C_1$-$C_4$-alkoxy, such as phenylamino-carbonylamino, p-toluylamino-carbonylamino, p-chlorophenylamino-carbonylamino and p-methoxyphenylamino-carbonylamino; alkylsulphonylamino radicals, especially those with 1-6 C atoms which can also be substituted, for example by hydroxyl or halogen, such as methylsulphonylamino, ethylsulphonylamino, n-butylsulphonylamino, ω-hydroxy-n-butylsulphonylamino, ω-chloro-n-propylsulphonylamino and n-hexylsulphonylamino; aralkylsulphonylamino radicals such as benzylsulphonylamino; arylsulphonylamino radicals, especially phenylsulphonylamino and naphthylsulphonylamino radicals which are optionally substituted by halogen, $C_1$-$C_4$-alkyl and $C_1$-$C_4$-alkoxy, such as phenylsulphonylamino, p-toluylsulphonylamino, m-chlorosulphonylamino, p-methoxyphenylsulphonylamino and 1-napthylsulphonylamino; 1,3,5-triazinylamino and 1,3,5-triazinyl-$C_1$-$C_3$-alkylamino, which can be substituted by halogen, $C_1$-$C_4$-alkoxy, phenoxy, phenyl, $C_1$-$C_4$-alkylmercapto, $C_1$-$C_4$-alkylamino, di-($C_1$-$C_4$-alkyl)-amino, morpholino and/or piperidino, such as 2,4-dichloro-triazinyl-6- amino, 2,4-dichloro-triazinyl-6-methylamino, 2,4-dichloro-triazinyl-6-ethylamino, 2,4-dichloro-triazinyl-6-n-propylamino, 2-di-β-hydroxyethylamino-4-chloro-triazinyl-6-amino, 2-n-propylamino-4-chloro-triazinyl-6-amino, 2-morpholino- or 2-piperidino-4-chloro-triazinyl-6-amino, 2-phenylamino-4-chloro-triazinyl-6-methylamino, 2-ethoxy-4 -chloro-triazinyl-6-amino, 2-phenoxy-4-chloro-triazinyl-6-amino, 2-phenyl-4-chloro-triazinyl-6-amino, 2-β-hydroxyethylmercapto-4-chloro-triazinyl-6-amino, 2,4-bis-diethylamino-triazinyl-6-amino and 2-methoxy-4-di-n-butylamino-triazinyl-6-amino; pyrimidylamino radicals, especially those which are substituted by halogen, such as 2,4-dichloropyrimidyl-6-amino, 2-fluoro-6-chloro-pyrimidyl-6-amino and 2,4-difluoro-5-chloro-pyrimidyl-6-amino; and also 2,3-dichloroquinoxaline-6-carbonylamino and -6-sulphonylamino radicals. Suitable alkylacylamino groups are those with 1-3 C atoms in the alkyl radical, with the acylamino radical having the abovementioned meaning.

By aryl radicals there are especially to be understood phenyl and naphthyl radicals which can in turn be substituted, especially by $C_1$-$CH_4$-alkyl radicals such as methyl, ethyl, isopropyl and t-butyl, by $C_1$-$C_4$-alkoxy radicals such as methoxy and ethoxy, halogen radicals such as chlorine and bromine, sulpho groups, $C_1$-$C_4$-alkylsulphonyl radicals such as methylsulphonyl and ethylsulphonyl, nitrile radicals, carboxylic acid $C_1$-$C_4$-alkyl esters such as the methyl esters or ethyl esters, or the carboxylic acid amide radical.

Suitable carboxylic acid ester radicals on aromatic radicals of which the remaining members are designated A are $C_1$-$C_4$-alkyl esters such as methyl, ethyl and isobutyl esters, carboxylic acid aralkyl esters such as the benzyl ester, and phenyl esters.

Suitable carboxylic acid amides and sulphonic acid amides as well as sulphonic acid amidines contain, for example, aryl groups such as phenyl, aralkyl groups such as benzyl and phenylethyl and especially alkyl groups; $C_1$-$C_8$-alkyl groups such as methyl, cyanomethyl, carboxymethyl, ethyl, β-hydroxyethyl, β-chloroethyl, n-butyl, isobutyl and n-hexyl may be singled out. Such alkyl radicals can also, together with the N atom to which they are bonded, form a saturated heterocyclic five-membered or six-membered ring such as pyrrolidine, piperidine, morpholine or N-$C_1$-$C_4$-alkyl-piperazine.

Preferred alkylsulphonyl radicals are methylsulphonyl and ethylsulphonyl radicals.

Possible heterocyclic radicals in A are, in addition to saturated nitrogen-containing 5-membered ring and 6-membered ring heterocyclic structures, such as pyrrolidine, piperidine, piperazine and morpholine, preferably aromatic five-membered ring heterocyclic structures such as pyrrole, pyrazole, 1,2,3-and 1,2,4-triazole, benztriazole, naphthtriazole, acenaphthtriazole, pyrazolotriazole, pyridotriazole, imidazole, benzimidazole, benzoxazole and benzthiazole.

Alkyl radicals R preferably have 1-6 C atoms and can in addition contain further radicals, for example hydroxyl, halogen such as chlorine or bromine, alkoxy such as methoxy or ethoxy, nitrile, carboxyl, carboxylic acid ester such as methyl ester, ethyl ester or β-methoxy-ethyl ester, β-hydroxyethyl ester or β-chloroethyl ester, δ-hydroxybutyl ester, isobutyl ester and benzyl ester, carboxylic acid amides, such as dimethylamide or diethylamide, amines such as dimethylamine or diethylamine or a saturated or aromatic five-membered or six-membered nitrogen-containing heterocyclic radical such as pyrrolidine, 1,2,4- or 1,2,3-triazole, piperidine, pyridine, morpholine and benzimidazole.

As examples of such alkyl radicals R there may be mentioned: methyl, ethyl, n-propyl, isopropyl, n-butyl, isobutyl, isoamyl, n-pentyl, n-hexyl, β-hydroxyethyl, methoxymethyl, β-ethoxyethyl, β-methoxyethyl, β-cyanoethyl, β-chloroethyl, β-bromoethyl, ω-chloro-n-propyl, β-carboxyethyl, β-methoxycarbonylethyl, β-ethoxycarbonylethyl, β-amidocarbonylethyl, β-diethylamidocarbonylethyl, 3-dimethylamino-n-propyl, β-morpholinylethyl, β-piperindinylethyl, β-1,2,3-triazolylethyl, β-pyridyl-(2)-ethyl and β-benzimidazolyl-(2)-ethyl.

The methyl and ethyl radical are particularly preferred.

Suitable aralkyl radicals R are phenylalkyl radicals with 1-4 C atoms in the alkyl radical, which are optionally substituted by halogen, $C_1$-$C_4$-alkyl or $C_1$-$C_4$-alkoxy. Preferred aralkyl radicals R are the benzyl, 4-chlorobenzyl, 4-methylbenzyl, 4-methoxybenzyl and β-phenylethyl radical.

As a cycloalkyl radical R, the cyclohexyl radical should especially be mentioned.

Suitable phenyl radicals R are phenyl radicals optionally substituted by halogen, $C_1$-$C_4$-alkyl or $C_1$-$C_4$-alkoxy, such as, for example, phenyl, p-toluyl, 4-methoxyphenyl or 4-ethoxyphenyl or 4-chlorophenyl.

Particularly preferred radicals R are alkyl radicals and benzyl radicals.

Alkylene radicals R which are cyclised with the naphthalene ring of the naphtholactam ring system in the 2-position preferably contain 2 to 3 C atoms.

Amongst the compounds of the formula I there may be mentioned, as a particularly valuable class, those which correspond to the formula II 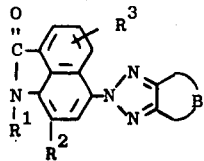

wherein
R$^1$ denotes hydrogen, alkyl, aralkyl, cycloalkyl or aryl or together with R$^2$ forms an alkylene radical,
R$^2$ represents hydrogen, alkyl, alkoxy, amino, nitro, halogen or sulpho,
R$^3$ denotes alkyl or alkoxy and
B represents the remaining members of a radical of the benzene series which can also be fused to a dioxole, dioxane, pyrazole or triazole ring, or the remaining members of a radical of the naphthalene series, to which a pyrrolidone ring can also be fused, or of the acenaphthene, anthracene, phenanthrene or pyrene series.

In detail, the comments made above apply to the substituents and radicals mentioned.

Amongst the compounds of the formula II there should in turn be especially singled out those which correspond to the formula IIa 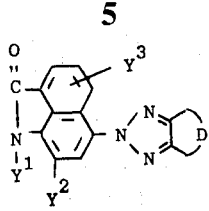

wherein
$Y^1$ denotes hydrogen, or a $C_1$-$C_5$-alkyl radical which is optionally substituted by chlorine, hydroxyl, nitrile, carboxyl, carboxylic acid $C_1$-$C_4$-alkyl ester or benzyl ester, carboxylic acid amide or $C_1$-$C_3$-alkoxy; a benzyl radical which is optionally substituted by $C_1$-$C_2$-alkyl, chlorine, $C_1$-$C_2$-alkoxy or nitrile; a phenyl radical which is optionally substituted by $C_1$-$C_2$-alkyl, chlorine or $C_1$-$C_2$-alkoxy, a cyclohexyl radical or, together with $Y^2$, a propylene radical, $Y^2$ represents hydrogen, chlorine, bromine, $C_1$-$C_3$-alkyl, $C_1$-$C_2$-alkoxy, amino or sulpho, $Y^3$ represents hydrogen or a $C_1$-$C_2$-alkoxy group and D represents the remaining members of a benzene radical which is optionally substituted by $C_1$-$C_4$-alkyl, $C_1$-$C_{12}$-alkoxy, amino, $C_1$-$C_4$-alkylamino, or di-($C_1$-$C_4$-alkyl)amino, a $C_1$-$C_6$-alkylcarbonylamino or -sulphonylamino radical which is optionally substituted by a $C_1$-$C_3$-N-alkyl radical, a phenylalkylcarbonylamino or phenylalkylsulphonylamino radical with 1-3 C atoms in the alkyl radical which is optionally substituted by halogen, a $C_1$-$C_4$-alkyl radical and/or $C_1$-$C_3$-N-alkyl radical, a benzoylamino, naphthoylamino, phenylsulphonylamino or naphthylsulphonylamino radidal which is optionally substituted by halogen, $C_1$-$C_4$-alkyl, $C_1$-$C_4$-alkoxy, nitrile, carboxylic acid $C_1$-$C_4$-alkyl ester and/or a $C_1$-$C_3$-N-alkyl radical, an alkylaminocarbonylamino or dialkylaminocarbonylamino radical with 1-4 C atoms in the particular alkyl radical, a phenylaminocarbonylamino radical which is optionally substituted by halogen, $C_1$-$C_4$-alkyl or $C_1$-$C_4$-alkoxy, a 1,3,5-triazinylamino or 1,3,5-triazinyl-$C_1$-$C_3$-alkylamino radical which is substituted by halogen, $C_1$-$C_4$-alkoxy, phenoxy, phenyl, $C_1$-$C_4$-alkylmercapto, $C_1$-$C_4$-alkylamino, di-($C_1$-$C_4$-alkyl)-amino, morpholino and/or piperidino, a pyrimidylamino radical which is substituted by halogen, the 2,3-dichloroquinoxaline-6-carbonylamino or -6-sulphonylamino radical, N-morpholinyl, N-piperidinyl, N-pyrrolidyl, N-pyrazolyl or N-triazolyl, it also being possible for a dioxole, dioxane or triazole ring to be fused to this benzene radical, the remaining members of a naphthalene radical which is optionally substituted by hydroxyl, $C_1$-$C_4$-alkoxy, $C_1$-$C_4$-alkyl, chlorine, bromine, nitrile, carboxyl, carboxylic acid $C_1$-$C_3$-alkyl ester, sulphonic acid, carboxylic acid amide or sulphonic acid amide optionally substituted by one or two $C_1$-$C_4$-alkyl radicals, an amino group optionally substituted by one or two $C_1$-$C_4$-alkyl radicals or a $C_2$-$C_3$-alkylcarbonylamino radical, it also being possible for a pyrrolidone ring to be fused to this naphthalene radical, and the remaining members of an acenaphthene, phenanthrene or pyrene radical which optionally contains sulpho groups.

A particularly valuable class of compounds of the formula IIa corresponds to the formula IIb 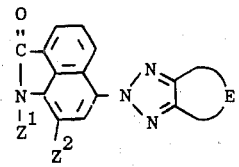

wherein
$Z^1$ denotes hydrogen, a $C_1$-$C_4$-alkyl radical which is optionally substituted by hydroxyl, chlorine or nitrile, or a benzyl radical, $Z^2$ represents hydrogen, methyl, ethyl or amino and E represents the remaining members of a benzene radical which can be substituted by $C_1$-$C_2$-alkyl, $C_1$-$C_4$-alkoxy, methylenedioxy, amino, $C_1$-$C_4$-alkylamino, $C_2$-$C_8$-dialkylamino, $C_1$-$C_4$-alkylcarbonylamino, $C_1$-$C_4$-alkylsulfonylamino, phenylacetylamino, benzylsulphonylamino, benzoylamino, naphthoylamino, phenylsulphonylamino, naphthylsulphonylamino or dichloro-1,3,6-triazinylamino radical (said acylamino groups are optionally substituted at the nitrogen atom by a $C_1$-$C_2$-alkyl group; the remaining members of a naphthalene radical which is optionally substituted by hydroxy, $C_1$-$C_3$-alkoxy, sulphonic acid, $C_1$-$C_2$-alkyl, amino, $C_1$-$C_2$-alkylamino or $C_2$-$C_4$-dialkylamino; or the remaining members of an acenaphthene or phenanthrene radical or pyrene radical which is optionally substituted by one or two sulpho groups. A A further valuable class of compounds within the scope of the general formula I corresponds to the formula III 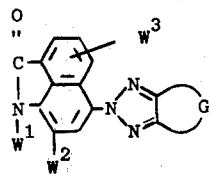

wherein
$W^1$ denotes hydrogen, alkyl, aralkyl, cycloalkyl or aryl or together with $W^2$ forms an alkylene radical, $W^2$ represents hydrogen, alkyl, alkoxy, amino, nitro, halogen or sulpho, $W^3$ denotes alkyl or alkoxy and G represents the remaining members of a radical of the pyridine, pyrazole or pyrimidine series.

Amongst the compounds of the formula III there should especially be singled out those which correspond to the formula IIIa 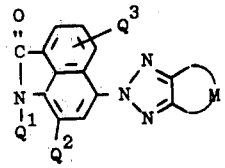

wherein
$Q^1$ denotes hydrogen, a $C_1$-$C_5$-alkyl radical which is optionally substituted by chlorine, hydroxyl, nitrile, carboxyl, carboxylic acid $C_1$-$C_4$-alkyl ester or benzyl ester, carboxylic acid amide or $C_1$-$C_3$-alkoxy, a benzyl radical which is optionally substituted by $C_1$-$C_2$-chlorine, $C_1$-$C_2$-alkoxy or nitrile, a phenyl radical which is optionally substituted by $C_1$-$C_2$- alkyl, chlorine or $C_1$-$C_2$-alkoxy, a cyclohexyl radical or, together with $Q^2$, a $C_3$-alkylene radical, $Q^2$ represents hydrogen, chlorine, bromine, $C_1$-$C_3$-alkyl, $C_1$-$C_2$-alkoxy, amino or sulpho, $Q^3$ represents hydrogen or a $C_1$-$C_2$-alkoxy group and M represents the remaining members of a pyrazole radical which can optionally be substituted by phenyl or naphthyl, which can also contain $C_1$-$C_2$-alkyl, methoxy, halogen, crboxyl or sulpho groups, or by a $C_1$-$C_2$-alkyl radical, or of a pyridine radical which is optionally substituted by amino, acetylamino, bromine, $C_1$-$C_2$-alkyl, carboxylic acid $C_1$-$C_2$-alkyl ester or carboxylic acid amide or of a pyrimidine radical which is optionally substituted by hydroxyl, $C_1$-$C_4$-alkyl, benzyl or phenyl radicals, it also being possible for the pyridine radical to be present as a quaternary salt.

Those compounds of the formula IIIa in which

M represents the remaining members of an α-aminopyridine radical, as well as their quaternary salts, are preferred.

A particularly valuable class of compounds of the formula IIIa corresponds to the formula IIIb 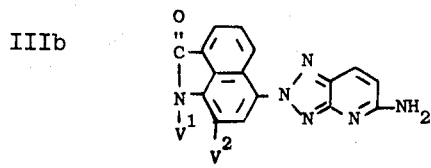

wherein $V^1$ denotes hydrogen, a $C_1$-$C_4$-alkyl radical which is optionally substituted by hydroxyl, chlorine or nitrile, or a benzyl radical and $V^2$ represents hydrogen, methyl, ethyl or amino, and their quaternary salts of the formula IV 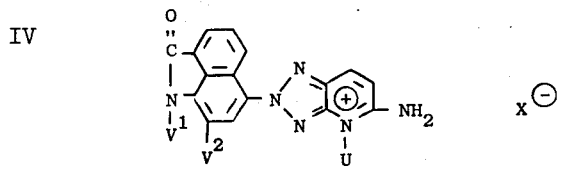

wherein $V^1$ and $V^2$ have the meaning indicated above (formula IIIb),

U represents a $C_1$-$C_4$-alkyl radical which is optionally substituted by $C_1$-$C_2$-alkoxy, hydroxyl, nitrile, carboxyl or carboxylic acid $C_1$-$C_2$-alkyl ester, or represents a benzyl radical which is optionally substituted by chlorine or methoxy and X denotes an anion.

Suitable anions are the organic and inorganic anions used in cationic dyestuffs.

Inorganic anions are, for example, radicals of hydrohalic acids, such as fluoride, chloride, bromide and iodide anions; the perchorate anion, the hydroxyl anion; radicals of sulphur-containing acids, such as hydrogen sulphate, sulphate, disulphate and aminosulphate anions; radicals of nitrogen-oxo acids, such as the nitrate anion; radicals of oxo acids of phosphorus, such as dihydrogen phosphate, hydrogen phosphate, phosphate and metaphosphate anions; radicals of carbonic acid, such as hydrogen carbonate and carbonate anions; further anions of oxo acids and complex acids, such as methosulphate ($CH_3SO_2O$), ethosulphate ($C_2H_5OSO_2O$), hexafluorosilicate, cyanate, thiocyanate, hexacyanoferrate (II), hexacyanoferrate (III), trichlorozincate, tetrachlorozincate, stannate, borate, divanadate, tetravanadata, molybdate, tungstate anions; complex anions of esters of boric acid with polyhydric alcohols, such as the glycerol ester of boric acid; and also the borotetrafluoride anion.

Organic anions are, for example, radicals of saturated or unsaturated aliphatic, cycloaliphatic, aromatic and heterocyclic carboxylic acids and sulphonic acids, such as formate, acetate, α-chloroacetate, α-cyanoacetate, α-hydroxyacetate, α-aminoacetate, α-methylaminoacetate, β-aminoethyl sulphonate, β-methylaminoethyl sulphonate, n-propionate, i-propionate, n-butyrate, i-butyrate, 2,2-dimethyl acetate, 2-methyl butyrate, 2-ethyl butyrate anions; the anions of dichloroacetic acid, trichloroacetic acid, trifluoroacetic acid, 2-chloropropionic acids, 3-chloropropionic acid, 2-chlorobutyric acid, 2-hydroxypropionic acids, 3-hydroxypropionic acid, lactic acids, glycollic acid, O-ethyl glycollic acid, thioglycollic acid, glyceric acid, malic acid, dodecyl tetraethylene glycol ether-propionic acid, 3-(nonyloxy)-propionic acid, 3-(isotridecyloxy)-propionic acid, 3-(isotridecyloxy)-diethylene glycol ether-propionic acid; ether-propionic acid of the alcohol mixture with 6 to 10 carbon atoms; cyanoacetic acid, thioacetic acid, 6-benzoylamino-2-chlorocaproic acid, nonyl-phenol tetraethylene glycol ether-propionic acid, nonyl-phenol diethylene glycol ether-propionic acid, dodecyl tetraethylene glycol ether-propionic acid, phenoxy-acetic acid, nonyl-phenoxyacetic acid, n-valeric acid, i-valeric acid, 2,2,2-trimethylacetic acid, n-caproic acid, 2-ethyl-n-caproic acid, stearic acid, palmitic acid, n-pelargonic acid, lauric acid; a mixture of aliphatic carboxylic acids with 9 to 11 carbon atoms (versatic acid 911 of SHELL); a mixture of aliphatic carboxylic acids with 15–19 carbon atoms (versatic acid 1519 of SHELL); the coconut fatty acid first runnings, undecane-carboxylic acid, n-tridecane-carboxylic acid and a coconut fatty acid mixture; acrylate and methacrylate anions; as well as the anions of crotonic acid and propargylic acid; furthermore, the anionic radicals of oxalic acid, malonic acid, succinic acid, glutaric acid, adipic acid, pimelic acid, suberic acid, azelaic acid; the isomer mixture of 2,2,4- and 2,4,4-trimethyl-adipic acid; sebacic acid, isosebacic acid (isomer mixture), tartaric acid, citric acid, glyoxylic acid, galactaric acid, dimethyl-ether-α,α'-dicarboxylic acid, methylene-bis-thioglycollic acid, dimethyl-sulphide-α,α'-dicarboxylic acid, 2,2'-dithio-di-n-propionic acid, fumaric acid, maleic acid, nitrilosulphonic acid $N(SO_3H_3)$ and itaconic acid, methane-sulphonic acid, ethane-sulphonic acid, chloromethane-sulphonic acid, 2-chloro-ethane-sulphonic acid, obtained by chlorosulphonation of paraffin oil.

Radicals of cyclic carboxylic acids are also suitable, such as the radicals of cyclohexane-carboxylic acid, cyclohexane-3-carboxylic acid; and also araliphatic monocarboxylic acids, such as phenylacetic acid, 4-methyl-phenylacetic acid, tolylic acid and mandelic acid.

Suitable means of aromatic carboxylic acids are, for example, the radicals of benzoic acid, 2-methylbenzoic acid, 3-methylbenzoic acid, 4-methylbenzoic acid, 4-tert-butylbenzoic acid, 2-bromobenzoic acid, 2-chlorobenzoic acid, 3-chlorobenzoic acid, 4- chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitrobenzoic acid, 2,4-dinitrobenzoic acid, 3,4-dinitrobenzoic acid, 3,5-dinitrobenzoic acid, 2-hydroxybenzoic acid, 2-mercapto-benzoic acid, 4-nitro-3-methylbenzoic acid, 4-aminobenzoic acid, 5-nitro-2-hydroxybenzoic acid, 3-nitro-2-hydroxybenzoic acid, 3-chloro-4-hydroxybenzoic acid, 5-chloro-2-hydroxy-3-methylbenzoic acid, 4-ethylmercapto-2-chlorobenzoic acid, 2-hydroxy-3-methylbenzoic acid, 6-hydroxy-3-methylbenzoic acid, 2-hydroxy-4-methylbenzoic acid, 6-hydroxy-2,4-dimethylbenzoic acid, 6-hydroxy-3-tert.-butylbenzoic acid, phthalic acid, tetrachlorophthalic acid, 4-hydroxyphthalic acid, 4-methoxyphthalic acid, isophthalic acid, 4-chloro-isophthalic acid, 5-nitro-isophthalic acid, terephthalic acid, nitroterephthalic acid, diphenylcarboxylic acid-(3,4), o-vanillic acid, 3-sulphobenzoic acid, benzene-tetracarboxylic acid-(1,2,4,5), naphthalene-tetracarboxylic acid-(1,4,5,8), biphenylcarboxylic acid-(4), abietic acid, phthalic acid-mono-n-butyl ester, terephthalic acid monomethyl ester, 3-hydroxy-5,6,7,8-tetrahydronaphthalene-carboxylic acid-(2), 2-hydroxy-naphthoic acid-(1) and anthraquinone-carboxylic acid-(2).

Suitable anions are also the radicals of heterocyclic carboxylic acids, for example, the radicals of benzene-sulphonic acid, benzene-disulphonic acid-(1,3), 4-chlorobenzene-sulphonic acid, 3-nitrobenzene-sulphonic acid, 6-chloro-3-nitrobenzene-sulphonic acid, toluene-sulphonic acid-(4), toluene-sulphonic acid-(2), toluene- -sulphonic acid, 2-chlorotoluene-sulphonic acid-(4), 1-hydroxybenzene-sulphonic acid, n-dodecyl-benzene-sulphonic acid, tetrapropylenebenzene-sulphonic acid-(6), naphthalene-sulphonic acid-(1), naphthalene-disulphonic acid-(1,4) or -(1,5), naphthalene-sulphonic acid-(2), naphthalene-sulphonic acid-(2,6), naphthalene-sulphonic acid-(2,7), or naphthalene-sulphonic acid-(1,3,6), naphthol-(1)-sulphonic acid-(2), 8-aminonaphthalene-sulphonic acid-(1), stilbene-disulphonic acid-(2,2'), biphenylsulphonic acid-(2).

Suitable heterocyclic sulphonic acids are, for example, the radicals of quinoline-sulphonic acid-(5).

Further suitable anions are those of the following acids: nitriloacetic acid, ethylene-bis-iminoacetic acid, benzene-sulphinic acid, benzene-phosphonic acid.

Colourless or almost colourless anions are preferred. For dyeing from an aqueous solution, those anions are preferred, which do not too strongly impair the solubility of the dyestuff in water. For dyeing from an aqueous dispersion this consideration is of no importance for the selection of the anions. For dyeing from organic solvents, those anions are also frequently preferred, which further the solubility of the dyestuff in organic solvents, or at least do not adversely affect it; the anions of organic mono- and di-carboxylic acids with 4 to 30 carbon atoms are to be mentioned in the first place.

The new naphtholactam compounds of the formula I are obtained, according to the invention, when o-aminoazo compounds of the formula

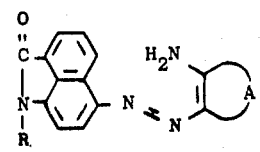   V wherein

A and R have the abovementioned meaning are dehydrogenated according to methods which are in themselves known, to give the corresponding triazole compound.

The triazolisation reaction is appropriately carried out analogously to the instructions of British Patent Specification 990,102, in a hydrophilic, non-oxidisable organic solvent, such as dimethylformamide, pyridine or a picoline mixture, by heating the o-aminoazo dyestuff of the formula V with a suitable oxidising agent, for example a copper-II salt such as copper-II sulphate, chloride, acetate, carbonate or naphthenate, in the presence of water and of nitrogen bases such as ammonia, diethanolamine or especially pyridine, or with an alkali metal hypochlorite, such as sodium hypochlorite.

The reaction is appropriately carried out in the temperature range of 20° – 90°.

A further form of carrying out the triazolisation consists of reacting the o-aminoazo dyestuff of the formula V, in accordance with the instructions of German Offenlegungsschrift (German Published Specification) 1,803,636, with thionylaniline compounds in high-boiling solvents such as dichlorobenzene, to give I.

The o-aminoazo compounds of the formula V are obtainable according to various processes. Thus, for example, o-nitro-amino compounds of the formula

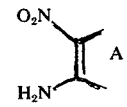   VI wherein

A has the abovementioned meaning can be diazotised and coupled to 1-naphthylamine-8-carboxylic acid; thereafter, the lactam ring can be closed by warming with an acid and the nitro group can be converted to the amino group by reduction.

A particularly suitable process for the manufacture of compounds of the formula V, which is also a subject of the invention within the framework of the manufacture of compounds of the formula I, consists of diazotising 4-amino-naphtholactam compounds of the formula

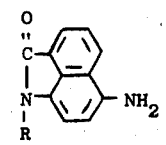   VII wherein

R has the abovementioned meaning and coupling the resulting diazonium compound to the o-position of an amino compound of the formula

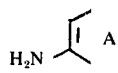　VIII wherein

A has the abovementioned meaning.

4-Amino-N-ethyl-naphtholactam-(1,8) (VII, R = $C_2H_5$) is known (German Auslegeschrift (German Published Specification) 1,190,126, Example 6) and is obtained by nitration of N-ethyl-naphtholactam-(1,8) at 0°–20° and subsequent reduction of the nitro compound with iron in aqueous acid suspension. The remaining compounds of the formula VII are manufactured analogously (from the corresponding amino-free compounds).

The diazotisation of the compounds of the formula XI is appropriately carried out in a solution strongly acidified with mineral aceid, for example sulphuric acid, at −5° to +10°C, by running in alkali metal nitrite solution and optionally stirring for several hours thereafter.

After destroying the excess nitrite and filtering, the diazonium salt solution thus obtained is coupled at a pH value of 3–8, preferably 5–6, in the temperature range of 0°–60°, the reaction first being carried out at 5°–15°C and the coupling then being completed by warming to 40°–60°. Coupling is appropriately carried out in an aqueous or aqueous-organic medium, for example in a mixture of water and pyridine, picoline bases, dimethylformamide or a urea solution.

As examples of suitable 4-amino-naphtholactam compounds of the formula VII there may be mentioned: 4-amino-naphtholactam-(1,8), 4-amino-N-methyl-naphtholactam-(1,8), 4-amino-N-ethyl-naphtholactam-(1,8), 4-amino-N-n-propyl-naphtholactam-(1,8), 4-amino-N-isopropyl-naphtholactam-(1,8), 4-amino-N-n-butyl-naphtholactam-(1,8), 4-amino-N-isobutyl-naphtholactam-(1,8), 4-amino-N-isoamyl-naphtholactam-(1,8), 4-amino-N-n-hexyl-naphtholactam, 4-amino-N-cyclohexyl-naphtholactam-(1,8), 4-amino-N-benzyl-naphtholactam-(1,8), 4-amino-N-(4'-chlorobenzyl)-naphtholactam-(1,8), 4-amino-N-(4'-methylbenzyl)-naphtholactam-(1,8), 4-amino-N-β-phenylethyl-naphtholactam-(1,8), 4-amino-N-phenyl-naphtholactam-(1,8), 4-amino-N-(4'-methoxyphenyl)-naphtholactam-(1,8), 4-amino-N-(4'-ethoxyphenyl)-naphtholactam-(1,8), 4-amino-N,2-trimethylene-naphtholactam-(1,8), 4-amino-N-(4'-methylphenyl)-naphtholactam-(1,8), 4-amino-N-β-cyanoethyl-naphtholactam-(1,8), 4-amino-N-β-methoxyethyl-naphtholactam-(1,8), 4-amino-N-β-chloroethyl-naphtholactam-(1,8), 4-amino-N-β-cyanoethyl-2-methoxy-naphtholactam, 4-amino-N-β-cyanoethyl-2-ethoxy-naphtholactam-(1,8), 4-amino-N-methoxycarbonylmethyl-naphtholactam-(1,8), 4-amino-N-β-dimethylamidocarbonylethyl-naphtholactam, 4-amino-N-β-ethoxycarbonylethyl-naphtholactam, 4-amino-N-β-dimethylaminoethyl-naphtholactam, 4-amino-N-β-morpholinyl-ethyl-naphtholactam-(1,8), 4-amino-N-β-piperidinylethyl-naphtholactam-(1,8), 4-amino-N-methyl-6-methoxy-naphtholactam, 4-amino-N-β-pyridyl-(2')-ethyl-naphtholactam-(1,8), 4-amino-N-β-benzimidazolyl-(2')-ethyl-naphtholactam-(1,8), 4amino-N-ethyl-2-bromo-naphtholactam-(1,8), 4-amino-N-ethyl-2-chloro-naphtholactam-(1,8), 4-amino-N-ethyl-naphtholactam-2-sulphonic acid, 4-amino-N-ethyl-2-methyl-naphtholactam-(1,8), 4-amino-N,2-diethyl-naphtholactam-(1,8), 4-amino-N-ethyl-7-methoxy-naphtholactam-(1,8), and 4-amino-N-methyl-phenanthrenolactam-(1,10). (1-Methyl-phenanthrenolactam-(1,10) is described in Chem. Soc. 1971, 3,357.)

As examples of suitable coupling components of the formula VIII there may be mentioned: aminobenzenes such as 1-amino-4-methyl-5-methoxybenzene, 1-amino-4-methyl-4-ethoxybenzene, 1-amino-4-methyl-5-n-butoxy-benzene, 1-amino-4-methyl-5-isopropoxy-benzene, 1-amino-4-methyl-5-sec. butoxy-benzene, 1-amino-4-methyl-5-isoamyloxy-benzene, 1-amino-4-methyl-5-n-octyloxy-benzene, 1-amino-4-ethyl-5-carboxymethoxy-benzene, 1-amino-4-methyl-5-n-dodecyloxy-benzene, 1-amino-4-methyl-5-β-hydroxyethoxy-benzene, 1-amino-4-methyl-5-β-ethoxyethoxy-benzene, 1-amino-4-methyl-5-β-carboxyethoxy-benzene, 1-amino-4-chloro-5-methoxy-benzene, 1-amino-4,5-dimethoxy-benzene, 1-amino-4,5-diisopropoxy-benzene, 1-amino-4,5-di-β-carboxyethoxy-benzene, 1-amino-4,5-methylenedioxy-benzene, 1-amino-4,5-dimethyl-benzene, 6-amino-benzdioxane-(1,3), 6-amino-benzdioxane-(1,4) and 4,4'-diamino-2,2'-dimethoxy-diphenyl; diaminobenzenes such as 1,3-phenylenediamine, 1,3-diamino-4-methyl-benzene, 1,3-diamino-4-methoxy-benzene, 1,4-diamino-3-methoxy-benzene, 1,3-diamino-4-chloro-benzene, N,N-dimethyl-1,3-phenylenediamine, N,N-diethyl-1,3-diaminobenzene, 3-acetamino-4-methyl-aniline and 3-n-propionylamino-4-methyl-aniline; aminonaphthalenes such as 2-aminonaphthalene, 2-amino-5-methoxynaphthalene, 2-amino-6-methoxynaphthalene, 2-amino-7-methoxynaphthalene, 1-amino-4-methylnaphthalene, 1-amino-4-methoxynaphthalene, 1-amino-4-ethoxynaphthalene, 1-amino-4-n-propoxynaphthalene, 1-amino-4-isopropoxynaphthalene, 1-amino-5-8-dichloronaphthalene, 1-amino-4-diethylaminonaphthalene, 1-amino-5-methylsulphonylnaphthalene, 2-amino-8-naphthol, 1-naphthylamine-4-sulphonic acid, 1-naphthylamine-5-sulphonic acid, 1-naphthylamine-4,8-disulphonic acid, 2-naphthylamine-1-sulphonic acid, 2-naphthylamine-6-sulphonic acid, 2-naphthylamine-3,6-disulphonic acid, 1-naphthylamine-4-sulphonamide, 1-naphthylamine-5-sulphonamide, 2-naphthylamine-6-sulphonamide, 1-naphthylamine-4-dimethylsulphonamide, 1-naphthylamine-5-diethylsulphonamide, 2-naphthylamine-6-diethylsulphonamide, 2-naphthylamine-7-methylsulphonamide, 1-naphthylamine-4-(3'-dimethylaminopropyl)-sulphonamide, 3-carboxy-2-aminonaphthalene-6-sulphonic acid, 6-ethoxycarbonyl-1(2)-naphthylamine and 2-sulphomethylaminonaphthalene; aminoacenaphthenes such as 4- or 5-aminoacenaphthene, 6-chloro-5-aminoacenaphthene and 6-methoxy-5-amino-acenaphthene; amino compounds of trinuclear and polynuclear aromatic hydrocarbons, such as 9-aminophenanthrene, 2-aminoanthracene and 3-aminopyrene, and the dipotassium salt of 2-aminoanthrahydroquinone-bis-sulphuric acid half ester; 5-aminopyrazoles such as 1-phenyl-3-methyl-5-aminopyrazole, 1-p-chloro-phenyl-3-methyl-5-aminopyrazole, 1-p-tolyl-3-methyl-5-aminopyrazole, 1-(8'-sulphonaphthyl-(2'))-3-methyl-5-aminopyrazole, 1-p-carboxyphenyl-3-methyl-5-aminopyrazole, 1-m-sulphophenyl-methyl-5-aminopyrazole and 1-cyanoethyl-3-methyl-5-aminopyrazole; aminopyridines such as 2,5-diaminopyridine, 2,6-diamino-3-methylpyridine, 2,6-diamino-4-methylpyridine, 2,6-diaminopyridine-4-carboxylic acid methyl ester, 2,6-diamino-3-bromopyridine, 2,6-diamino-4-bromo-pyridine and 2,6-diamino-pyridine-4-carboxylic acid amide; aminopyrimidines such as 4-amino-2,6-dihydroxy-pyrimidine; aminoindazoles such as 5- or 6-aminoindazole; aminobenztriazoles such as 2-phenyl-5-amino-benztriazole, 2-(p-cyanophenyl)-5-amino-benztriazole, 2-(p-methoxyphenyl)-5-amino-benztriazole, 2-phenyl-6-chloro-5-amino-benztriazole, 2-phenyl-6-methyl-5-amino-benztriazole, 2-phenyl-6-methoxy-5-amino-benztriazole, 2-α-naphthyl-5-amino-benztriazole, 5-(p-chlorophenyl)-5-amino-benztriazole and 2-(p-sulphophenyl)-5-amino-benztriazole; and amino-benz[c,d]-indoles such as 4-amino-N-ethyl-naphtholactam-(1,8), 4-amino-N-methyl-naphtholactam-(1,8), 4-amino-N-β-cyanoethyl-naphtholactam-(1,8) and 4-aminocoumarine.

Compounds of the formula I which in addition to the triazole nitrogen atoms shown in the general formula I contain at least one tertiary quaternisable nitrogen atom can be converted into quaternary dyestuff salts by reaction with quaternising agents - within the scope of the formula I.

Examples of such tertiary groupings containing quaternisable nitrogen are dialkylamino groups or N-heterocyclic structures such as morpholine, piperidine, pyrrolidine, imidazole, benzimidazole, 1,2,3-triazole, 1,2,4-triazole, thiazole or pyridine. Compounds of the formula I in which A represents the remaining members of a pyridine radical should be singled out as being particularly suitable for a quaternisation.

Examples of suitable quaternising agents are alkyl halides such as methyl iodide, ethyl bromide, n-propyl bromide, i-propyl chloride, allyl bromide, n-butyl bromide, isoamyl chloride, sulphuric acid esters of lower alkanols such as dimethylsulphate, diethylsulphate or dimethyl pyrosulphate, aromatic sulphonic acid esters such as p-toluenesulphonic acid methyl ester, ethyl ester, β-chloroethyl ester and β-cyanoethyl ester, m-chlorobenzenesulphonic acid ethyl ester and substituted alkyl halides such as β-chloropropionitrile, 3-dimethylamino-n-propyl chloride, 4-hydroxybutyl bromide, phenylethyl bromide, benzyl chloride, p-chlorobenzyl chloride, p-methoxy-benzyl chloride, p-cyanobenzyl chloride, 2-bromo-diethyl ether, bromacetic acid methyl ester, β-chloropropionic acid ethyl ester, β-bromopropionic acid dimethylamide, ethylene oxide, propylene oxide or glycidyl methyl ether in glacial acetic acid or vinyl pyridine in formic acid. Dimethylsulphate and diethylsulphate are particularly preferred.

The new naphtholactam compounds of the formula I are predominantly yellow to red crystalline powders which dissolve in organic media, especially solvents such as alcohols, esters, amides, lower fatty acids, ethers and ketones to give an intense yellow-green to lemon-yellow fluorescence. The naphtholactam compounds containing sulpho groups, or quaternary salts, also dissolve in water.

The naphtholactam compounds of the formula I are valuable dyestuffs or dyestuff intermediate products. They are outstandingly suitable for dyeing oils and for bulk-dyeing of macromolecular organic materials such as lacquers, films, sheets, fibres and mouldings, for example those of cellulose esters such as cellulose 2½-acetate and triacetate, polyvinyl compounds such as polyvinyl chloride and polyvinyl acetate, polyurethanes, polystyrene, polyesters and polycarbonates, in very clear, brilliant, predominantly luminous yellow shades. For this end use it is in particular possible to employ the compounds of the formula I which are not salt-like, as well as those compounds containing sulpho groups which are in the form of salts of suitable organic cations such as, for example, of alkylamines which confer lipid solubility or those quaternary salts which are in the form of salts of suitable organic anions which confer lipid solubility.

These compounds can also be milled into the materials mentioned together with pigment dyestuffs, especially yellow pigments, whereby a substantial improvement in appearance is achieved.

A further preferred field of use for the naphtholactam dyestuffs according to the invention, of the formula I, is the dyeing and printing of natural and synthetic fibre and fabric materials. Whilst the dyestuffs containing sulpho groups are particularly suitable for dyeing polyamide, polyurethane and wool fibres, particularly good effects and fastness properties are obtained on polyester fibres and fabrics with the dyestuffs which are not salt-like.

Materials which are particularly suitable for dyeing with the basic dyestuffs amongst those of the formula I are flocks, fibres, filaments, tapes, woven fabrics or knitted fabrics of polyacrylonitrile or of copolymers of acrylonitrile with other vinyl compounds such as vinyl chloride, vinylidene chloride, vinyl fluoride, vinyl acetate, vinylpyridine, vinylimidazole, vinyl alcohol, acrylic acid esters and methacrylic acid esters and acrylic acid amides and methacrylic acid amides, and asymmetrical dicyanoethylene, or flocks, fibres, filaments, tapes, woven fabrics or knitted fabrics of acid-modified aromatic polyesters and of acid-modified polyamide fibres. Acid-modified aromatic polyesters are, for example, polycondensation products of sulphoterephalic acid and ethylene glycol, that is to say polyethylene glycol terephthalates containing sulphonic acid groups (type Dacron 64 of E. I. DuPont de Nemours and Company) such as are described in Belgian Pat. specification No. 546,179 and U.S. Pat. Specification No. 2,893,816.

Using the dyestuffs according to the invention, of the formula I, very brilliant dyeings in greenish-tinged to reddish-tinged yellow shades, which fluoresce yellow-green to yellow in ultraviolet light and daylight, are produced on the fibres and fabrics mentioned; the dyeings are distinguished by good build-up and affinity and by good fastness properties such as fastness to washing, rubbing, sublimation, perspiration and flue gas and, for fluorescent dyestuffs, very good fastness to light and heat stability. The fact that they are largely insensitive to changes in pH value should also be singled out.

The compounds hitherto proposed as fluorescent yellow dyestuffs do not possess these advantageous properties to the same extent.

The dyestuffs according to the invention, of the formula I, can be used for dyeing and printing in accordance with customary processes, for example in the form of aqueous solutions, dispersions or printing pastes. The dye baths and printing pastes can contain the customary dyeing auxiliary additives such as levelling agents, dispersing agents and dyeing accelerators, for example substituted polyglycol ethers, condensation products of aromatic sulphonic acids and formaldehyde, condensation products of higher-molecular aliphatic amines and ethylene oxide, higher-molecular alkyl sulphates and alkyl sulphonates in the form of their aqueous sodium salts or cyclohexylamine salts, condensation products of higher-molecular alcohols and ethylene oxide, cellulose sulphite waste liquor products, o-hydroxydiphenyl, halogenated aromatic hydrocarbons and/or esters of aromatic carboxylic acids.

The dyestuffs according to the invention can also advantageously be used for dyeing from organic solutions, for example from solutions in which water-immiscible solvents such as tetrachloroethylene, trichloroethylene, 1,1,2-trichloroethane or 1,1,1-trichloropropane are used.

Basic dyestuffs of the formula I are suitable for dyeing mouldings of polymers or copolymers of acrylonitrile, asymmetrical dicyanoethylene, acid-modified aromatic polyesters or acid-modified synthetic polyamides, from chlorinated hydrocarbons as the dye bath, if the dyestuffs carry substituents which assist the solubility in chlorinated hydrocarbons, for example the tertiary butyl group, or if An⁻ is the anion of a monobasic organic acid with 4 – 30 carbon atoms. Examples of such organic salts are: 2-ethylcaproic acid, lauric acid, oleic acid, linoleic acid, a mixture of aliphatic carboxylic acids with 15 – 19 carbon atoms (Versatic Acid 1,519), a mixture of aliphatic carboxylic acids with 9 – 11 carbon atoms (Versatic Acid 911), coconut fatty acid first runnings, tetradecanoic acid, undecylenic acid, dimethylpropanoic acid, dimethylacetic acid, carboxylic acids of which the carbon chain is interrupted by hetero-atoms, such as nonylphenol-tetraethylene glycol-ether-propionic acid, nonylphenol-diethylene glycol-ether-propionic acid, dodecyl-tetraethylene glycol-ether-propionic acid, 3-(nonyloxy)-propionic acid, 3-(isotridecyloxy)-propionic acid, 3-(isotridecyloxy)-diethylene glycol-ether-propionic acid, the ether-propionic acid of an alcohol miture with 6 – 10 carbon atoms, nonylphenoxyacetic acid, aromatic carboxylic acids such as tert.-butyl-benzoic acid, cycloaliphatic carboxylic acids such as hexahydrobenzoic acid, cyclohexenecarboxylic acid, abietic acid and sulphonic acids such as tetrapropylenebenzenesulphonic acid.

Basic dyestuffs of the formula (I) in which one of the acids listed here forms the anion are preferred. If the basic dyestuffs are in the form of salts of the monobasic organic acids with 4 – 30 carbon atoms which have been mentioned, concentrated solutions, of good stability, of these dyestuffs in chlorinated hydrocarbons can be prepared, if appropriate with addition of polar organic solvents which are completely miscible with chlorinated hydrocarbon, such as butyrolactam, dimethylformamide methanol, dioxane, acetonitrile, methyl ethyl ketone, nitrobenzene, dimethylsulphoxide, benzonitrile and 2-nitrochlorobenzene.

To manufacture such solutons, the methane dyestuffs according to the invention, in the form of salts of organic acids with 4–30 carbon atoms, are stirred in, if appropriate with addition of polar organic solvents which are completely miscible with chlorinted hydrocarbons, and if appropriate at elevated temperature.

Basic dyestuffs of the formula (I) form light-fast pigments, which can advantageously be employed in paper printing, with anionic precipitants such as alumina, tannin, phosphotungstic acids and phosphomolybdic acids.

In the examples which follow, parts are to be understood as parts by weight. The temperature data are degrees Centigrade.

EXAMPLE 1

42.4 parts of 4-amino-N-ethyl-naphtholactam-(1,8) are suspended in 250 parts by volume of water and 80 parts by volume of 36% strength hydrochloric acid and 0.5 parts of tributyl phosphate as an anti-foaming agent are added whilst stirring. About 62 parts by volume of 30% strength by volume sodium nitrite solution is allowed to run in slowly, whilst cooling externally with ice and whilst stirring, until an excess of nitrite persists. The suspension is stirred for a further 3 hours at 0° whilst maintaining an excess of nitrite, the excess nitrite is destroyed with amidosulphonic acid, the ice-cold diazonium salt solution is filtered and is subsequently slowly run into a solution of 27.4 parts of 1-amino-4-methyl-5-methoxy-benzene in 520 parts of water and 12 parts of 36.5% strength hydrochloric acid at about 5° – 15°, and at the same time saturated sodium acetate solution is added so as always to maintain a pH value of 5 – 6. After stirring for a further hour at 10°–25° the crystalline red dyestuff is filtered off, washed with water and pressed out well.

The dyestuff, whilst still moist, is introduced into 900 parts by volume of pyridine. 180 parts of crystalline copper sulphate and 200 parts by volume of water are added whilst stirring and the mixture is heated to the boil under reflux for 1 hour. It is then poured out onto 6,000 parts by volume of water. The crystalline precipitate is filtered off, washed with water and recrystallised from 600 parts by volume of toluene, the water being removed azeotropically and the solution subsequently clarified with 6 parts of Tonsil. 27 parts of the compound of the formula (1) 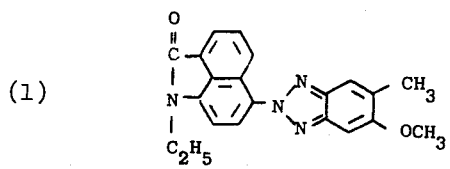

are obtained. The compound dissolves in toluene to give a strongly greenish-tinged yellow colour and a green-yellow fluorescence.

If instead of 1-amino-4-methoxy-benzene the equivalent amount of 6-amino-benzdioxane-(1,3) is employed, 24 parts of the compound of the formula (2) 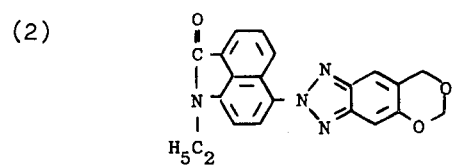

are obtained; this compound dissolves in toluene to give a strongly greenish-tinged yellow colour and a green-yellow fluorescence.

The following compounds are manufactured in an analogous procedure, using the appropriate starting compounds:

Table

Compounds of the formula

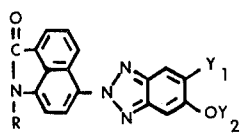

| Compound No. | R | $Y_1$ | $Y_2$ | Colour of solution in toluene | Colour of fluorescence in toluene |
|---|---|---|---|---|---|
| (3) | $C_2H_5$ | $CH_3$ | $C_2H_5$ | strongly greenish-tinged yellow | green-yellow |
| (4) | $NC-CH_2-CH_2$ | $CH_3$ | $-CH(CH_3)_2$ | " | " |
| (5) | $CH_3$ | $CH_3$ | $-CH_2-CH(CH_3)_2$ | " | " |
| (6) | H | $CH_3$ | $-(CH_2)_3-CH_3$ | " | " |
| (7) | $C_6H_5-$ | $CH_3$ | $-CH_2-COOH$ | " | " |
| (8) | $C_6H_5-CH_2-$ | $CH_3$ | $-(CH_2)_{11}-CH_3$ | " | " |
| (9) | $C_2H_5$ | $CH_3$ | $-C_2H_4-O-C_2H_5$ | " | " |
| (10) | $CH_3(CH_2)_3-$ | Cl | $-CH_2-CH_2-OH$ | " | " |

EXAMPLE 2

42.4 parts of 4-amino-N-ethyl-naphtholactam-(1,8) are diazotised in accordance with the instructions of Example 1. 31 parts of 4-amino-veratrol are suspended in 300 parts by volume of water and dissolved by adding 30 parts by volume of 36% strength hydrochloric acid. The solution is cooled to 10° and the diazonium salt solution is added over the course of 20 minutes at 15°. A pH value of 5 – 6 is maintained constantly by simultaneously running in sodium acetate solution. After stirring for a further 2 hours at 15° – 20° the crystalline precipitate is filtered off, washed with water and well pressed out.

The dyestuff, whilst still moist, is introduced into 800 parts by volume of pyridine. 180 parts of crystalline copper sulphate and 120 parts by volume of water are added whilst stirring and the mixture is heated to the boil under reflux for 1 hour and is poured out at 60° into 6,000 parts of water. The crystalline precipitate is filtered off, washed with water and dried in vacuo at 60°. 31 parts of the compound of the formula

(11)
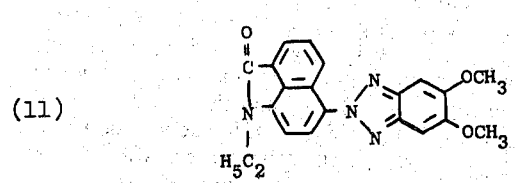

are obtained.

The compound is purified by recrystallisation from 180 parts of methylglycol, subsequent hot extraction with methylcyclohexane, recrystallisation of the evaporation residue from 200 parts of toluene and clarification with 4 parts of Tonsil. The compound dissolves in toluene to give a greenish-tinged yellow colour and green-yellow fluorescence.

If instead of 4-amino-veratrol the equivalent amount of 1-amino-4,5-diisopropoxybenzene is employed, 49 parts of compound of the formula

(12)
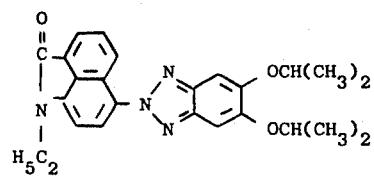

are obtained. The compound purified by hot extraction with methylcyclohexane and recrystallisation from toluene also dissolves in toluene to give a greenish-tinged yellow colour and green-yellow fluorescence.

The following compounds are manufactured analogously, using the appropriate starting compounds:

(13)
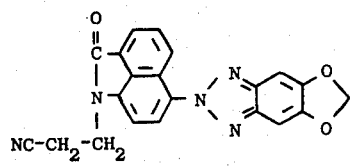

(14) [structure: naphtholactam with N-CH2-phenyl, linked via N=N to benzodioxine]

(15) [structure: naphtholactam N-H, linked via N=N to benzene with two OCH2-CH2-COOH groups]

All three substances dissolve in dimethylformamide to give a yellow colour and green-yellow fluorescence.

EXAMPLE 3

106 parts of 4-amino-N-ethyl-naphtholactam-(1,8) are diazotised in accordance with the instruction of Example 1. 115 parts of 2-naphthylamine-1-sulphonic acid are dissolved in 1,500 parts by volume of water whilst adding 500 parts by volume of saturated sodium acetate solution and the mixture is clarified, whilst cold, with 3 parts of active charcoal. The diazonium salt solution is allowed to run slowly into this solution at 10° – 15° whilst stirring, the pH being kept in the range of 4 – 5 by simultaneous further addition of saturated sodium acetate solution (a total of 3,500 parts by volume). Thereafter the reaction mixture is stirred for a further 2 hours, whilst allowing the temperature to rise to room temperature. The crystalline red dyestuff is filtered off, washed with water and pressed out well.

The dyestuff, whilst still moist, is introduced into 900 parts by volume of pyridine. A solution of 300 parts of crystalline copper sulphate in 200 parts by volume of water is added whilst stirring and the mixture is heated to 85° – 90° over the course of 30 minutes and kept at this temperature for 30 minutes. The crystalline precipitate is filtered off at 15°, washed with water and dried in vacuo at 30°. 62 parts of the compound of the formula

(16) [structure: naphtholactam with N-C2H5, linked to naphthotriazole]

are obtained. After twice recrystallising from toluene, using Tonsil, the compound is pure. It dissolves in toluene to give a greenish-tinged yellow colour and green-yellow fluorescence.

The following compounds are manufactured analogously using the appropriate starting compounds:

Table

Compounds of the formula

[structure: naphtholactam-N(R) linked via N=N to naphthotriazole]

| Compound No. | R | Colour of solution in benzene | Colour of fluorescence in benzene |
|---|---|---|---|
| (17) | $CH_3-$ | greenish-tinged yellow | green-yellow |
| (18) | $CH_3-(CH_2)_3-$ | " | " |
| (19) | phenyl-$CH_2-$ | " | " |
| (20) | cyclohexyl- | " | " |
| (21) | phenyl- | " | " |
| (22) | $C_2H_5O$-phenyl- | " | " |
| (23) | $Cl-CH_2-CH_2-$ | " | " |
| (24) | $NC-CH_2-CH_2-$ | " | " |
| (25) | $HOOC-CH_2-CH_2-$ | " | " |
| (26) | $Cl$-phenyl-$CH_2-$ | " | " |

EXAMPLE 4

42.4 parts of 4-amino-N-ethyl-naphtholactam-(1,8) are diazotised in accordance with the instructions of Example 1. 52.6 parts of 2-naphthylamine-7-sulphonic acid hydrochloride are dissolved in 1,000 parts of water whilst warming and the solution is cooled to 15°C. The diazonium salt solution is allowed to run slowly into this solution at 15° – 20° and at the same time saturated sodium acetate solution is added in such a way as always to maintain a pH value of 5 – 6. After stirring for a further 2 hours at room temperature, the crystalline red dyestuff is filtered off, washed with 5% strength sodium chloride solution and well pressed out.

The dyestuff, whilst still moist, is introduced into 800 parts by volume of pyridine. 180 parts of crystalline copper sulphate and 150 parts by volume of water are added whilst stirring, the mixture is heated to the boil under reflux for 10 minutes and the solvent is subsequently removed by distilling off in vacuo. The residue is taken up in 1,000 parts of hot water. After cooling, the crystalline precipitate is filtered off, washed with water until the water issues colourless, twice recrystallised, in each case from 500 parts by volume of dimethylformamide and using 5 parts of active charcoal, washed with methanol and dried at 70° in vacuo.

42 parts of the compound of the formula

(27) 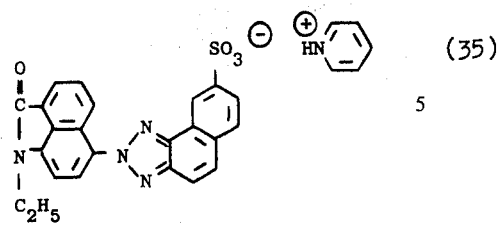  (35) 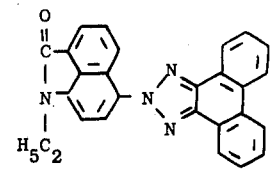

are obtained. The compound dissolves in dimethylformamide or glacial acetic acid to give a yellow colour and green-yellow fluorescence. It also gives a yellow solution in water but with only a weak greenish-yellow fluorescence. Treatment of (27) with 2 N sodium hydroxide solution or potassium hydroxide solution and salting out with NaCl or KCl yields the corresponding alkali metal salts. The following compounds are manufactured by an analogous procedure, using the appropriate starting compounds:

are obtained. The compound is purified by hot extraction with methylcyclohexane, evaporation of the solvent in vacuo and recrystallisation of the evaportion residue from toluene, using Tonsil. The compound dissolves in toluene to give a yellow colour and shows a green-yellow fluorescence.

If instead of 9-amino-phenanthrene an equivalent amount of 5-amino-acenaphthene is employed, 52 parts of the compound of the formula Table Compounds of the formula

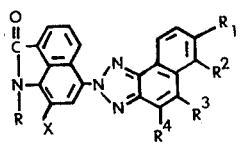

| Compound No. | R | X | R¹ | R² | R³ | R⁴ | Solution/fluorescence colour in glacial acetic acid | |
|---|---|---|---|---|---|---|---|---|
| 28 | $C_2H_5$ | H | $SO_3K$ | H | H | H | greenish-tinged yellow | green-yellow |
| 29 | $NC-CH_2-CH_2-$ | H | H | $SO_3Na$ | H | H | " | " |
| 30 | $CH_3$ | Br | H | H | $SO_3Na$ | H | " | " |
| 31 | ⌬–$CH_2-$ | H | $SO_3Na$ | H | H | COOH | " | " |
| 32 | $CH_3(CH_2)_3-$ | H | $SO_2N(C_2H_5)_2$ | H | H | H | " | " |
| 33 | $(CH_3)_2CH-$ | H | H | $SO_2-N\!\!\diagup\!\!O$ | H | H | " | " |
|  |  |  |  | $SO_2-N\!\!\diagup$ |  |  |  |  |
| 34 | $CH_3O-CH_2-CH_2-$ | Cl | H |  | H | H | " | " |

EXAMPLE 5

42.4 parts of 4-amino-N-ethyl-naphtholactam-(1,8) are diazotised according to the instructions of Example 1. 38.6 parts of 9-amino-phenanthrene are dissolved in 2,000 parts by volume of pyridine at room temperature. The diazonium salt solution is allowed to run into this solution at room temperature. After stirring for 3 hours at 20° – 25°, 180 parts of crystalline copper-II sulphate and 150 parts of crystalline copper-II sulphate and 150 parts of water are added and the mixture is heated to the boil under reflux for 5 hours and is poured out into 6,000 parts of water whilst stirring. The crystalline precipitate is filtered off, washed with water and dried in vacuo at 60°C. 58 parts of the compound of the formula

(36) 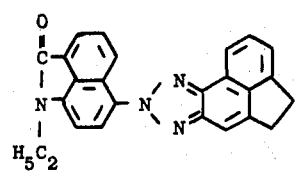

are obtained. After hot extraction with methylcyclohexane and recrystallisation from toluene, a solution of the substance in toluene shows a yellow colour and a green-yellow fluorescence.

The following compounds are obtained by an analogous procedure using the appropriate starting compounds:

| | Colour of solution | Colour of fluorescence in toluene |
|---|---|---|
| (37) | greenish-tinged yellow | green-yellow |
| (38) | yellow | green-yellow |
| (39) | yellow | green-yellow |
| (40) | yellow | green-yellow |
| (41) | greenish-tinged yellow | green-yellow |
| (42) | reddish-tinged yellow | green-yellow |

EXAMPLE 6

10 parts of the compound of the formula (35) (Example 5) are introduced into 40 parts of 96% strength sulphuric acid at 10°–15° and the mixture is stirred for a further hour at the indicated temperature. 10 parts of 25% strength oleum are now added dropwise at 15°–20° and the mixture is stirred for some hours longer at 30°–40° until a sample is completely soluble in hot water. The reaction mixture is poured out onto 100 parts of ice and 100 parts of water and the crystalline precipitate is filtered off, taken up in 100 parts of water, neutralised with sodium hydroxide solution, salted out by adding 30 parts of 10% strength sodium chloride solution, filtered off, washed with 5% strength sodium chloride solution and dried in vacuo at 60°. 13 parts of compounds of the formula

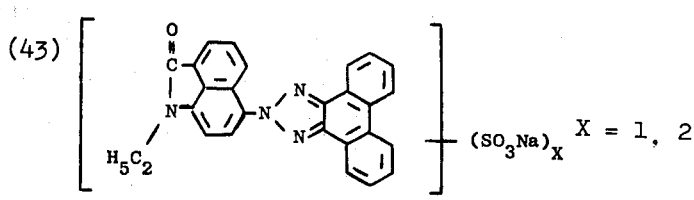

are obtaind as a yellow-red crystalline powder which dissolves in water to give a greenish-tinged yellow colour and a greenish-yellow fluorescence.

Analogous compounds are obtained if instead of compound 35) one of the other compounds mentioned in Example 5 is employed.

EXAMPLE 7

42.4 parts of 4-amino-N-ethyl-naphtholactam-(1,8) are diazotised in accordance with the instructions of Example 1. A further 42.4 parts of 4-amino-N-ethyl-naphtholactam are dissolved in 750 parts of pyridine whilst warming. The clarified diazonium salt solution is allowed to run into this solution at room temperture. After stirring for a further 3 hours, 180 parts of crystalline copper sulphate and 150 parts of water are added and the mixture is heated to the boil under reflux for 4 hours and is then poured out onto 6,000 parts of water. The crystalline precipitate is filtered off, washed with water and dried in vacuo at 60°. 96 parts of the compound of the formula

(44) 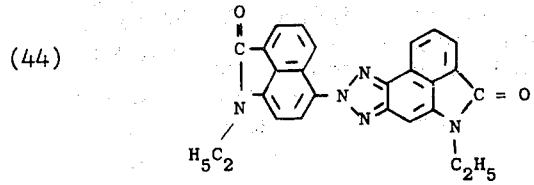

are obtained and are purified by recrystallisation from chlorobenzene, clarifying with Tonsil, washing with methanol and drying. In chlorobenzene, the compound shows a yellow solution colour and a greenish-yellow fluorescence. The following compounds are manufactured by an analogous procedure using the appropriate starting compounds:

EXAMPLE 8

42.4 parts of 4-amino-N-ethyl-naphtholactam-(1,8) are diazotised in accordance with the instructions of Example 1. 42 parts of 2-phenyl-5-amino-benztriazole are dissolved in 700 parts by volume of pyridine whilst warming, the solution is cooled, and the ice-cold filtered diazonium salt solution is slowly added at room temperature whilst stirring. After stirring for a further hour, 180 parts of crystalline copper sulphate are added to the mixture and the whole is heated to the boil for 2 hours whilst stirring and is poured out onto 6,000 parts of water. The crystalline precipitate is filtered off, washed with water and dried in vacuo at 60°. 63 parts of the compound of the formula

(48) 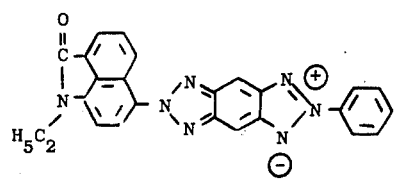

are obtained are are purified by recrystallisation from 600 parts of dimethylformamide, washing with methanol and drying. In toluene, they show a greenish-tinged yellow solution colour and green-yellow fluorescence.

If instead of 4-amino-N-ethyl-naphtholactam-(1,8) an equivalent amount of 4-amino-N-n-butyl-naphtholactam is diazotised and in other respects exactly the procedure indicated is followed, 61 parts of the compound of the formula

(49) 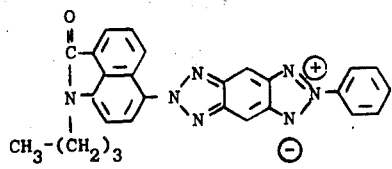

| Solution colour | Fluorescence colour |
|---|---|
| yellow (in DMF) | green-yellow |
| yellow (in DMF) | green-yellow |
| greenish-tinged yellow (in DMF) | green-yellow |

(45) 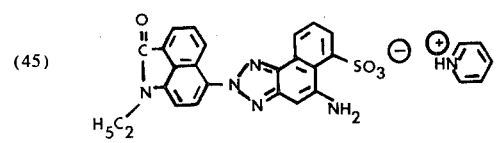

(46) 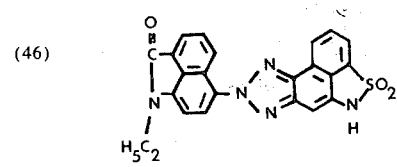

(47) 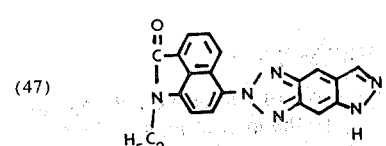

are obtained, and are purified by recrystallisation first from dimethylformamide and then from toluene (Tonsil) and again show a greenish-tinged yellow solution colour, and green-yellow fluroescence in toluene.

If, on the other hand, instead of 2-phenyl-5amino-benztriazole an equivalent amount of 2-(4'-methyl-phenyl)-5-amino-benztriazole is employed, 67 parts of the compound of the formula

(50) 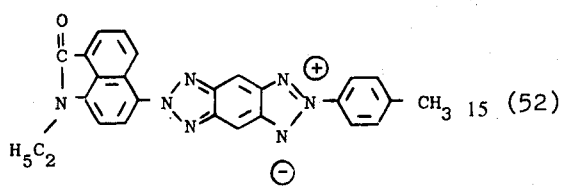

are obtained, which are purified by twice recrystallising from toluene (clarifying with Tonsil) and possess colour and fluorescence properties similar to compound (48).

If instead of 2-phenyl-5-amino-benztriazole an equiv-

(53) 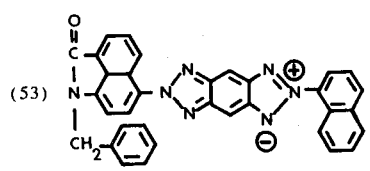

(54) 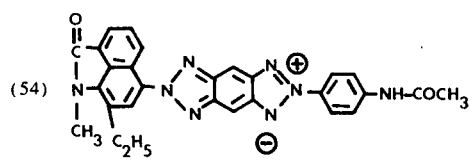

(55) 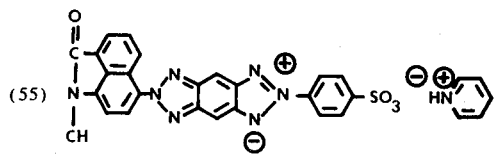

alent amount of 2-(4'-chlorophenyl)-5-amino-benztriazole is employed, 62 parts of the compound of the formula

(51) 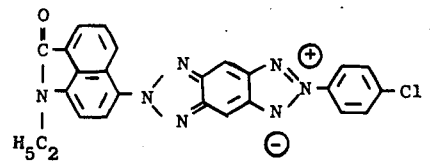

are obtained, and are purified by recrystallisation firstly from toluene (clarifying with Tonsil) and then from chlorobenzene. In toluene, they show a greenish-tinged yellow solution colour and a green-yellow fluorescence colour.

If instead of 2-phenyl-5-amino-benztriazole an equivalent amount of 2-(4'-methoxy-phenyl)-5-amino-benztriazole is employed, 65 parts of the compound of the formula

(52) 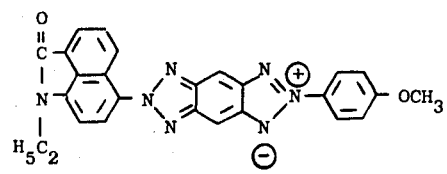

are obtained, which are purified by twice recrystallising from toluene (clarifying with Tonsil). They dissolve in toluene to give a greenish-tinged yellow colour and green-yellow fluorescence.

Further, the following compounds are obtained analogously from the appropriate starting compounds:

| | Solution colour | Fluorescence |
|---|---|---|
| | greenish-tinged yellow | green-yellow |
| | (toluene) | |
| | greenish-tinged yellow | green-yellow |
| | (toluene) | |
| | greenish-tinged yellow | greenish-yellow |
| | (in water) | |

EXAMPLE 9

42.2 parts of 4-amino-N-ethyl-naphtholactam-(1,8) are diazotised according to the instructions of Example 1. 40 parts of 1,3-diaminobenzene dihydrochloride are dissolved in 200 parts of water and the solution is cooled to 10°. The diazonium salt solution is allowed to run into this solution over the course of 30 minutes, at 10° – 20°. At the same time, saturated sodium acetate solution is added in such a way that the pH value is constantly kept between 5 and 6. After stirring for a further 6 hours, the crystalline precipitate is filtered off, washed with water and dried in vacuo at 50°. 56 parts of dyestuff of the formula

(56) 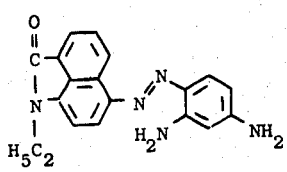

are obtained. 33 parts of this compound are treated with 350 parts of pyridine, 90 parts of crystalline copper sulphate and 100 parts of water and the mixture is heated to 80° for 30 minutes whilst stirring and is then poured out onto 4,000 parts of water. The crystalline precipitate is filtered off, washed with water and dried in vacuo at 60°. 22 parts of the compound of the formula

(57) 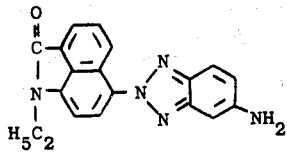

are obtained and are purified by hot extraction with methylcyclohexane, evaporation and recrystallisation of the evaporation residue from dichlorobenzene (clarifying with Tonsil). The substance dissolves in DMF to give a yellow colour, but without fluorescence. On the other hand it has a green-yellow fluroescence in chlorobenzene.

If instead of 1,3-diaminobenzene dihydrochloride an equivalent amount of 1,3-diamino-4-methoxy-benzene monosulphate or 1,4-diamino-3-methoxy-benzene monosulphate is employed, 26 and 28 parts of compound of the formula

(58) 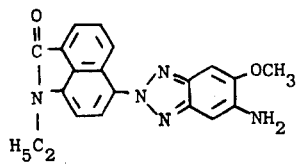

are respectively obtained and are purified by twice recrystallising from dichlorobenzene (clarifying with Tonsil). The substance dissolves in chlorobenzene to give a yellow colour and green-yellow fluroescence.

If instead of 1,3-diaminobenzene dihydrochloride and equivalent amount of N,N-dimethyl-1,3-phenylenediamine dissolved in dilute hydrochloric acid is employed, 31 parts of compound of the formula

(59) 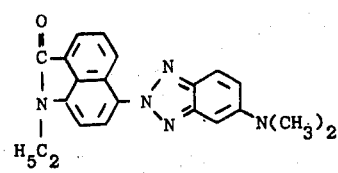

are obtained analogously, and are purified by hot extraction with methylcyclohexane, clarifying the extract with Tonsil, evaporation of the filtrate and recrystallisation of the evaporation residue from ethanol. In chlorobenzene, the compound shows a yellow solution colour and a green-yellow fluorescence.

Analogous compounds are also obtained if instead of 1,3-diaminobenzene dihydrochloride equivalent amounts of N,N-diethyl-1,3-phenylenediamine, 1,3-diamino-4-chlorobenzene, 1,3-diamino-4-methylbenzene, 3-acetamino-4-methyl-aniline and 3-n-propionylamino-4-methyl-aniline, dissolved in dilute hydrochloric acid, are employed.

EXAMPLE 10

15 parts of compound of the formula (57) are warmed with 130 parts of acetic anhydride to 50° for 30 minutes whilst stirring, and the mixture is then cooled. The yellow crystalline precipitate is filtered off, washed with methanol and dried in vacuo at 70°.

70 parts of compound of the formula

(60) 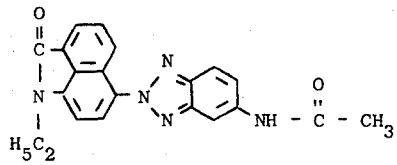

are obtained. The compound dissolves in chlorobenzene to give a greenish-tinged yellow colour and green-yellow fluorescence. In contrast to compound (57), it also fluoresces in dimethylformamide.

Analogous acylamino compounds are obtained if instead of compound (57) an equivalent amount of compound (58) or one of the compounds manufactured from 1,3-diamino-4-methylbenzene or 1,3-diamino-4-chlorobenzene according to Example 9 is employed.

Analogous acylamino compounds are also obtained if compound (57) or (58), instead of being reacted with acetic anhydride, is reacted with trifluoroacetic anhydride, β-chloropropionyl chloride, n-butyroyl chloride, β-chloroethylsulphonyl chloride, β-chloroacryloyl chloride, 2,2,3,3-tetrafluorocyclobutane-1-carboxylic acid chloride, benzoyl chloride, p-methoxybenzoyl chloride, p-toluoyl chloride, p-toluenesulphochloride, terephthaloyl dichloride, phenacetyl chloride, 2,3-dichloroquinoxaline-6-carboxylic acid chloride or thiophene-2-carboxylic acid chloride.

EXAMPLE 11

1.85 parts of cyanuric chloride are dissolved in 100 parts by volume of acetone and 50 parts of comminuted ice are added whilst stirring. A solution of 3.3 parts of the compound of the formula (57) in 160 parts by volume of acetone is allowed to run into the fine suspension thus obtained over the course of 15 minutes, whilst cooling with ice and stirring, and the hydrochloric acid liberated is neutralised by dropwise addition of 15% strength aqueous sodium carbonate solution. After the addition of (57), the luminous yellow suspension is stirred for a further 3 hours at 0° – 5° whilst keeping it neutral with sodium carbonate solution and is poured out into 400 parts of ice water, and the product is filtered off and dried in vacuo. 5 parts of the compound of the formula

(61) 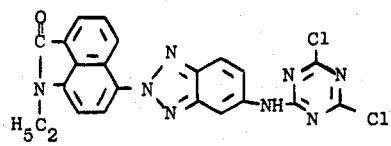

are obtained.

If the further reaction of (61) with diethylamine is desired, it is expedient to dispense with pouring out into ice water and isolating the product. An approximately 50% strength aqueous solution of 1.6 parts of diethylamine is introduced over the course of 30 minutes at 0° – 5° whilst stirring and the resulting mixture is stirred for a further 12 hours at 20° – 25°. To complete the reaction, the batch is further heated for 1 hour to 50° and is then cooled to 5° – 10°. The crystalline precipitate is filtered off, treated with 10% strength sodium acetate solution, washed with water and dried in vacuo at 60°. 5.5 parts of the compound of the formula

(62) 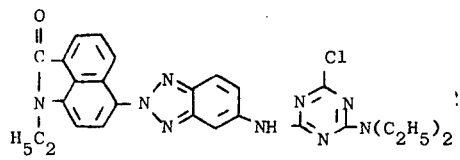

are obtained. The compound dissolves in dimethylformamide to give a yellow colour and green-yellow fluorescence. The following compounds are obtained analogously from the appropriate starting components:

EXAMPLE 12

1.85 parts of cyanuric chloride are dissolved in 100 parts by volume of acetone and 50 parts of comminuted ice are added whilst stirring. A solution of 3.3 parts of the compound of the formula (57) in 160 parts by volume of acetone is run into the fine suspension thus obtained over the course of 15 minutes, whilst cooling with ice and stirring and the hydrochloric acid liberated is neutralised by dropwise addition of 15% strength aqueous sodium carbonate solution. After the addition of (57), the suspension is stirred for a further 3 hours at 0° – 5° whilst keeping it neutral with sodium carbonate solution. Thereafter a solution of 3.3 parts of (57) in 160 parts by volume of acetone is again added at 0° – 10° and the mixture is warmed to 40° – 45° over the course of 15 minutes, whilst constantly maintaining a pH value of 6 – 7 by addition of 15% strength sodium carbonate solution. The pH value is also kept constant at 6 – 7 by means of sodium carbonate solution during the subsequently post-stirring time of 4 hours at 45° – 50°. 500 parts by volume of water at 40° are then added and the batch is stirred for 15 minutes at 40°. The crystalline precipitate is filtered off, washed with water and dried in vacuo at 70°. 7.8 parts of the compound of the formula

(71) 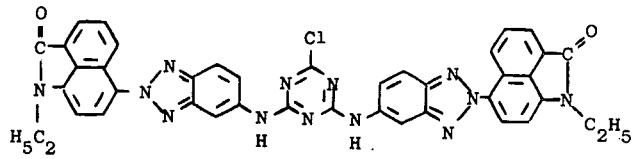

Table

Compounds of the formula

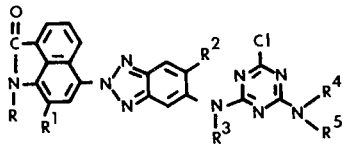

| Compound No. | R | R¹ | R² | R³ | R⁴ | R⁵ | colour of solution | Colour of fluorescence | Solvent |
|---|---|---|---|---|---|---|---|---|---|
| 63 | $CH_3$ | $C_2H_5$ | $CH_3$ | H | $HO-CH_2-CH_2-$ | H | yellow | green-yellow | DMF |
| 64 | $NC-CH_2-CH_2-$ | H | H | $CH_3$ | n-Butyl | n-Butyl | " | " | " |
| 65 | $C_6H_5-CH_2-$ | H | $OCH_3$ | H | \multicolumn{2}{c}{$N<^{R^4}_{R^5}$ = Morpholine} | " | " | " |
| 66 | $CH_3-(CH_2)_3-$ | H | H | $C_2H_5$ | H | $C_2H_5$ | " | " | " |
| 67 | $(CH_3)_2CH-$ | H | H | H | $NC-CH_2-CH_2-$ | $NC-CH_2-CH_2-$ | " | " | " |
| 68 | $C_2H_5-$ | H | H | H | $C_6H_5CH_2-$ | $C_6H_5CH_2-$ | " | " | " |
| 69 | H | H | H | H | $C_6H_5-$ | $CH_3$ | " | " | " |
| 70 | $CH_3-$ | Br | H | H | $C_6H_{11}-$ | $CH_3$ | " | " | " | are obtained. The compound is sparingly soluble in the customary organic solvents. In N-methylpyrrolidone it shows a yellow solution colour and a green-yellow fluorescence.

EXAMPLE 13

6.6 parts of the compound of the formula (57) and 10 parts of 2,4-bis-diethylamino-6-chloro-1,3,5-triazine in 50 parts by volume of dimethylformamide are heated to the boil for 8 hours whilst stirring under reflux, and the mixture is cooled and stirred with 50 parts by volume of alcohol. The crystalline precipitate is filtered off, washed with alcohol and dried in vacuo at 50°. 11 parts of the compound of the formula are obtained. The compound also dissolves in chlorobenzene to give a yellow colour and green-yellow fluorescence.

The following compounds are manufactured analogously, using the appropriate starting materials:

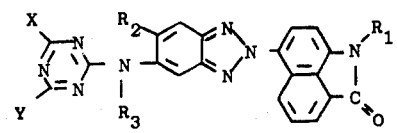

| Compound No. | X | Y | $R_1$ | $R_2$ | $R_3$ | Colour of solution (in chlorobenzene) | Colour of fluorescence |
|---|---|---|---|---|---|---|---|
| 74 | $N(CH_3)_2$ | $N(CH_3)_2$ | $C_6H_5CH_2$— | Cl | H | greenish-tinged yellow | green-yellow |
| 75 | NH—⟨H⟩ | NH—⟨H⟩ | —$(CH_2)_3CH_3$ | H | H | " | " |
| 76 | -N⟨⟩O | N⟨⟩O | $CH_2$—$CH_2$—CN | H | H | " | " |
| 77 | -N⟨⟩$SO_2$ | -N⟨⟩$SO_2$ | H | H | $C_2H_5$ | " | " |
| 78 | —NH($C_4H_9$) | —NH—$C_4H_9$ | ⟨⟩ | H | H | " | " |
| 79 | -NH-$CH_2$⟨⟩ | -NH-$CH_2$⟨⟩ | $CH_2$—$CH_2$—$CH_3$ | $CH_3$ | H | " | " |
| 80 | -NH⟨⟩ | -NH⟨⟩ | $C_2H_5$ | H | H | " | " |
| 81 | —$NH_2$ | —$NH_2$ | H | H | $CH_3$ | " | " |
| 82 | —NH—$CH_2$—$CH_2$OH / $CH_2CH_2OH$ | —NH—$CH_2$—$CH_2$OH / $CH_2$—$CH_2$OH | $C_2H_5$ | H | H | " | " |
| 83 | —N⟨ $CH_2CH_2OH$ | —N⟨ $CH_2$—$CH_2$OH | $C_2H_5$ | H | H | " | " |
| 84 | -N⟨⟩ | —$N(C_2H_5)_2$ | $C_2H_5$ | H | H | " | " |
| 85 | —O—$CH_3$ | —O—$CH_3$ | $C_2H_5$ | H | H | " | " |
| 86 | —$OC_6H_5$ | —$NH_2$ | $C_2H_5$ | H | H | " | " |
| 87 | —$OC_2H_5$ | —$OC_2H_5$ | $C_2H_5$ | H | H | " | " |
| 88 | —$OCH_2$—$CH_2$—$OCH_3$ | —$OCH_2$—$CH_2$—$OCH_3$ | $C_2H_5$ | H | H | " | " |
| 89 | —$N(CH_2CH_2CN)_2$ | —$N(CH_2$—$CH_2$—$CN)_2$ | $C_2H_5$ | H | H | " | " |
| 90 | —$NH_2$ | —NH—$(CH_2)_3CH_3$ | $C_2H_5$ | H | H | " | " |
| 91 | $N(C_2H_5)$ | OH | $C_2H_5$ | H | H | " | " |

(72) 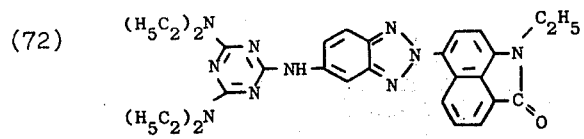

are obtained. The dyestuff dissolves in chlorobenzene to give a yellow colour and green-yellow fluorescence.

If instead of compound (57) an equivalent amount of compound (58) is employed, 12 parts of the compound of the formula

(72) 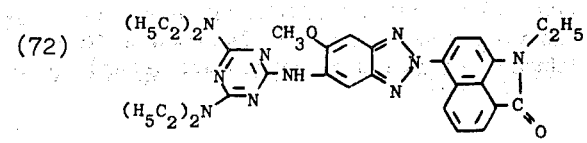

EXAMPLE 14

33 parts of the compound of the formula (57) are suspended in 200 parts by volume of water, 40 parts by volume of 36% strength hydrochloric acid are added whilst stirring and the mixture is diazotised with 30% strength by volume hydrochloric acid whilst cooling at 0° – 5°. The diazonium salt solution is filtered and poured, whilst stirring, into a sodium sulphite suspension which has been manufactured by neutralising 60 parts by volume of 38% strength technical sodium bisulphite solution with sodium hydroxide solution and diluting with 50 parts of water. The mixture is stirred for 3 hours at pH 6 and room temperature and is then treated with 60 parts by volume of 36% strength hydrochloric acid and stirred for a further 3 hours at 90°. After cooling to 20°, the crystalline precipitate is filtered off and dried. 34 parts of the compound of the formula

(91) 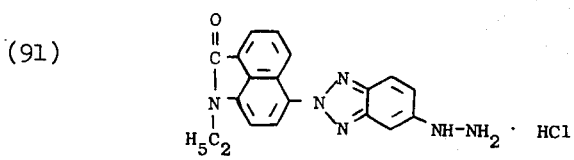 · HCl are obtained. 13.4 parts of this compound are stirred with a solution of 4 parts of anhydrous sodium acetate in 40 parts of water at 50°. A solution of 6 parts of oximinoacetophenone in 50 parts by volume of ethanol is added at pH 5.5 and the mixture is warmed, whilst stirring, for 3 hours to 75° at pH 5.5 – 5.2. Thereafter 100 parts of water are added and the crystalline precipitate is filtered off at room temperature, washed with water and dried at 50° in vacuo.

14.7 parts of the α-oximinohydrazone obtained are dissolved in 25 parts by volume of dimethylformamide and 20 parts by volume of pyridine. 5 parts by volume of acetic anhydride are slowly run into this solution and the mixture is heated for 2 hours to 110° and a further 2 hours to 125°, the solvent is stripped off in vacuo and the residue is diluted with 40 parts by volume of methanol. The crystalline precipitate is filtered off and twice recrystallised from dimethylformamide. 7 parts of compound of the formula

(93) 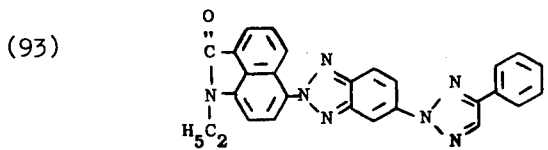

are obtained. The compound dissolves in chlorobenzene to give a yellow colour and green-yellow fluorescence. The following compounds are obtained analogously using the appropriate starting materials:

(98) 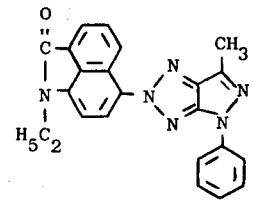

are obtained. It shows a yellow solution colour and green-yellow fluorescence colour in chlorobenzene.

EXAMPLE 15

42.4 parts of 4-amino-N-ethyl-naphtholactam-(1,8) are diazotised in accordance with the instructions of Example 1. 34.6 parts of 1-phenyl-3-methyl-5-amino-pyrazole are dissolved in 740 parts of water whilst adding 60 parts by volume of 36% strength hydrochloric acid and warming. The resulting solution is cooled to 15° and the ice-cold, filtered diazonium salt solution is then added at 15° – 20° over the course of 30 minutes. At the same time, saturated sodium acetate solution is adde dropwise in such a way as constantly to maintain a pH value of 5 – 6. After stirring for 2 hours at room temperature, the red-yellow crystalline precipitate is filtered off, washed with water and firmly pressed out.

The dyestuff, whilst still moist, is taken up in 750 parts by volume of pyridine, 180 parts of crystalline copper sulphate and 150 parts of water are added and the mixture is heated for 30 minutes to the boil under reflux and poured out onto 6,000 parts of water. The crystalline precipitate is filtered off, washed with water and dried in vacuo at 70°.

51 parts of the compound of the formula

(99) 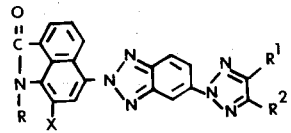

Table

Compounds of the formula

| Compound No. | R | X | R¹ | R² | Colour of solution (in chlorobenzene) | Colour of fluorescence |
|---|---|---|---|---|---|---|
| 94 | CH₃ | C₂H₅ | C₆H₅ | C₂H₅ | yellow | green-yellow |
| 95 | NC—CH₂—CH₂ | H | COOC₂H₅ | CH₃ | " | " |
| 96 | C₆H₅CH₂ | H | C₂H₅ | CH₃ | " | " |
| 97 | (CH₃)₂CH— | H | ⌬-CH₂ | C₂H₅ | " | " |

If 7.6 parts of the compound of the formula (91) are condensed with 2.4 parts of 1,1-dimethoxy-acetone for 2 hours in boiling n-propanol, 7 parts of the compound of the formula are obtained and are purified by recrystallisation from 600 parts of toluene (clarifying with 8 parts of Tonsil and washing with methanol). The solution colour in toluene is yellow and the fluorescence colour is green-yellow.

If instead of 1-phenyl-3-methyl-5-amino-pyrazole an equivalent amount of 1-(8'-sulphonaphthyl-(2')-3-methyl-5-amino-pyrazole dissolved in 1,000 parts of water is employed, with addition of sodium hydroxide solution and sodium acetate solution (pH 6), recrystallisation from 1,000 parts of glacial acetic acid, washing with acetonitrile and drying yields 31 parts of the compound of the formula This disslves in water or glacial acetic acid to give a yellow colour and greenish-yellow fluorescence.

Analogously to what has been indicated for compound (99), the use of equivalent amounts of the appropriate starting compounds yields the following compounds:

| | Solution colour (toluene) | Fluorescence (toluene) |
|---|---|---|
| (101) 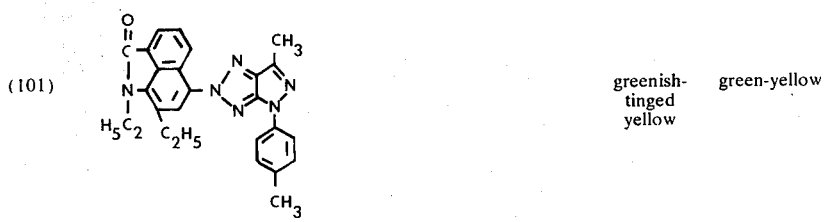 | greenish-tinged yellow | green-yellow |
| (102) 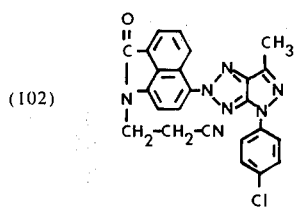 | '' | '' |
| (103) 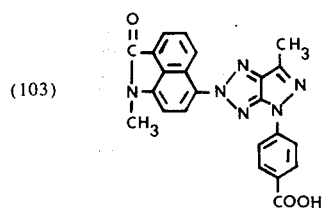 | '' | '' |
| (104) 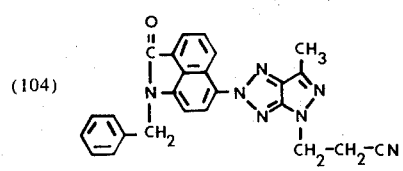 | '' | '' |

(100) 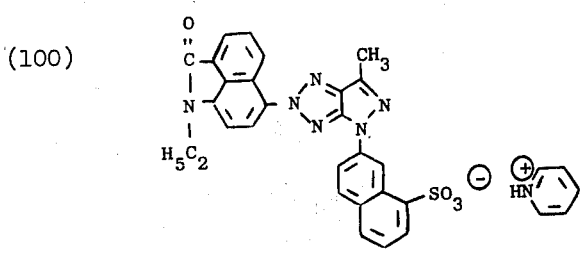

EXAMPLE 16

36.8 parts of 4-amino-naphtholactam-(1,8) are suspended in 250 parts by volume of water and 80 parts by volume of 36% strength hydrochloric acid are added whilst stirring. About 62 parts by volume of 30% strength by volume sodium nitrite solution are slowly allowed to run in under the surface at 0°, whilst cooling with ice, until an excess of nitrite persists. The mixture is stirred for a further 15 minutes at 0°, the excess nitrite is destroyed with amidosulphonic acid and the ice-cold diazonium salt solution is filtered and is subsequently run into a solution of 35 parts of 1-phenyl-3-methyl-5-amino-pyrazole in 1,000 parts of pyridine over the course of 15 minutes. After stirring for a further 2 hours at room temperature, 180 parts of crystalline copper sulphate are added and the mixture is heated to 80° – 85° for 2 hours whilst stirring and is then cooled to 20°. The crystalline precipitate is filtered off, washed with water until the water issues colourless and dried in vacuo at 70°. 65 parts of compound of the formula (105) 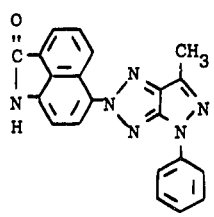

are obtained. The substance is purified by recrystallisation, first from 1,400 parts by volume of dimethylformamide and then from 1,100 parts by volume of o-dichlorobenzene. It dissolves in dimethylformamide to give a greenish-tinged yellow colour and green-yellow fluorescence.

Analogous compounds are obtained if instead of 1-phenyl-3-methyl-5-amino-pyrazole an equivalent amount of one of the following substances is employed: 1-(p-chlorophenyl)-3-methyl-5-amino-pyrazole, 1-p-tolyl-3-methyl-5-amino-pyrazole, 1-p-carboxyphenyl-3-methyl-5-amino-pyrazole, 1-cyanoethyl-3-methyl-5-amino-pyrazole and 1,3-diphenyl-5-amino-pyrazole.

3 parts of the compound of the formula (105), 30 parts of acrylonitrile and 2 parts of triethylene diamine are heated for 20 hours to the boil under reflux, whilst stirring. After cooling, the crystalline precipitate is filtered off, washed with methanol and dried in vacuo at 50°. 3.5 parts of the compound of the formula (106) 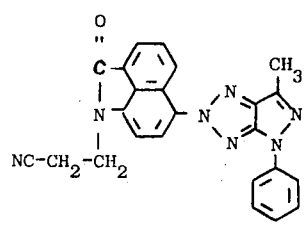

are obtained. The compound is purified by recrystallisation from dimethylformamide and then shows a greenish-yellow solution colour and green-yellow fluorescence in dimethylformamide.

EXAMPLE 17

7.3 parts of the compound of the formula (105) are suspended in 70 parts by volume of dimethylformamide. 1.15 parts of powdered potassium hydroxide are added, whilst excluding water, whereupon the suspension assumes a luminous red colour. Thereafter 3 parts of dimethyl sulphate are added dropwise over the course of 10 minutes whilst stirring at 40° – 45° and cooling, whereupon the red colouration changes to yellow. After stirring for a further 10 minutes, the addition of KOH and of dimethyl sulphate is repeated. The mixture is then diluted with 200 parts of water. The crystalline precipitate is filtered off, washed with water and dried. 8 parts of the compound of the formula (107) 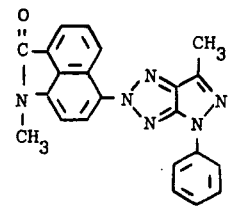

are obtained. This dissolves in dimethylformamide to give a greenish-tinged yellow colour and yellow-green fluorescence.

The reaction of compound (105) with the alkylating agents listed in the table which follows is carried out analogously:

Table

| Alkylating agent | Reaction Temperature | Compound No. | Colour of solution | Colour of fluorescence |
|---|---|---|---|---|
| | | | (in DMF) | |
| Diethyl sulphate | 40–50° | (99) | greenish-tinged yellow | green-yellow |
| Isopropyl bromide | 60° | (108) | " | " |
| n-Butyl bromide | 60° | (109) | " | " |
| Benzyl chloride | 50–60° | (110) | " | " |
| p-Chlorobenzyl chloride | 60° | (111) | " | " |
| p-Methoxybenzyl chloride | 60° | (112) | " | " |
| p-Methylbenzyl chloride | 60° | (113) | " | " |
| Isoamyl bromide | 60° | (114) | " | " |

To convert into the β-hydroxyethyl compound, 18.3 parts of the compound (105) are dissolved in 120 parts of dimethylformamide, 0.5 part of powdered potassium hydroxide is added and about 2.5 parts of ethylene oxide are injected in an autoclave at 120°. After 4 hours the mixture is cooled and diluted with water. The crystalline precipitate is filtered off, washed with water and recrystallised from propanol. 16 parts of the compound of the formula (115) 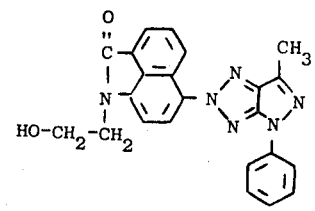

are obtained. This dissolves in dimethylformamide to give a yellow colour and green-yellow fluorescence. The reaction with propylene oxide (instead of ethylene oxide) is carried out analogously.

EXAMPLE 18

63.6 parts of 4-amino-N-ethyl-naphtholactam-(1,8) are diazotised in accordance with the instructions of Example 1. 32.7 parts of 2,6-diamino-pyridine are dissolved in 500 parts by volume of glacial acetic acid and 1,500 parts of water and 60 parts by volume of 36% strength hydrochloric acid are added. The ice-cold diazonium salt solution is allowed to run into this solution over the course of 15 minutes. A pH value of about 5 is maintained by simultaneously running in a saturated sodium acetate solution. The mixture is stirred for a further 2 hours. The crystalline red coupling dyestuff is filtered off and dried in vacuo at 60°. 55 parts of compound of the formula (116) 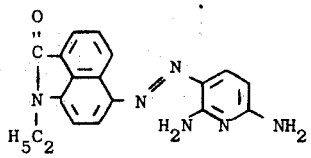

are obtained as a red crystal powder. This is suspended in 350 parts of pyridine, mixed with 162 parts of crystalline copper sulphate and 100 parts by volume of water and heated to 90° – 95° for 30 minutes. After cooling, the crystalline precipitate is filtered off, washed with water and dried in vacuo at 70°. 35 parts of compound of the formula (117) 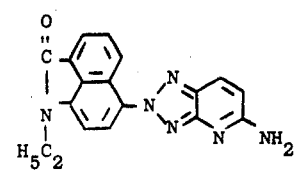

are obtained. The compound is purified by recrystallisation from o-dichlorobenzene (clarifying with Tonsil). The substance dissolves in toluene to give a yellow colour and green-yellow fluorescence. If instead of 4-amino-N-ethyl naphtholactam-(1,8) the equivalent amount of 4-amino-naphtholactam-(1,8) is employed (the diazotisation instruction is given in Example 16), 44 parts of the compound of the formula (118) 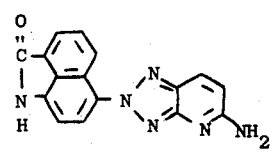

are obtained. This dissolves in dimethylformamide to give a yellow colour and green-yellow fluorescence. Analogous compounds are obtained if instead of 2,6-diamino-pyridine equivalent amounts of the following compounds are employed: 2,6-diamino-3-bromo-pyridine, 2,6-diamino-4-bromo-pyridine, 2,6-diamino-3-methyl-pyridine, 2,6-diamino-4-methyl-pyridine, 2,6-diamino-pyridine-4-carboxylic acid methyl ester, 2,6-diamino-pyridine-4-carboxylic acid and 4-amino-2,6-dihydroxy-pyrimidine.

The following compounds are also obtained in an analogous manner, using the appropriate starting materials:

Compounds of the formula

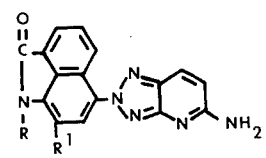

| Compound No. | R | R¹ | Colour of solution in toluene | Colour of fluorescence |
|---|---|---|---|---|
| (119) | CH₃ | C₂H₅ | yellow | green-yellow |
| (120) | R + R¹ = | —CH₂—CH₂—CH₂— | '' | '' |
| (121) | HO—CH₂—CH₂— | H | '' | '' |
| (122) | NC—CH₂—CH₂ | Br | '' | '' |
| (123) | HO—CH—CH₂—  CH₃ | H | '' | '' |
| (124) | ⌬—CH₂ | CH₃O | '' | '' |
| (125) | ⌬— | H | '' | '' |
| (126) | ⌬(H)— | H | '' | '' |
| (127) | CH₃—(CH₂)₃ | H | '' | '' |
| (128) | CH₃\CH—/CH₃ | Cl | '' | '' |

-continued

Compounds of the formula

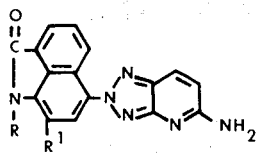

| Compound No. | R | R¹ | Colour of solution | Colour of fluorescence in toluene |
|---|---|---|---|---|
| (129) | HOOC—$CH_2$—$CH_2$— | H | " | " |
| (130) | $CH_3$OOC—$CH_2$— | H | " | " |

EXAMPLE 19

1.4 parts of the compound of the formula (117) and 15 parts by volume of acetic anhydride are briefly heated to the boil, diluted with 3 parts by volume of acetone and cooled. The crystalline precipitate is filtered off, washed with acetone and dried in vacuo at 70°. 1.3 parts of the compound of the formula (131) 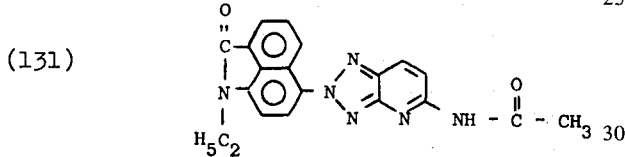

(mixed melting point with (117) shows a strong depression) are obtained. (131) dissolves in toluene to give a yellow colour and green-yellow fluorescence. Analogous acylamino compounds are obtained if (117) or one of the analogous compounds indicated in Example 18 is reacted with one of the following acylating agents instead of acetic anhydride: trifluoroacetic anhydride, n-butyroyl chloride, β-chloropropionyl chloride, β-chloroethylsulphonyl chloride, 2,2,3,3-tetrafluorocyclobutane-1-carboxylic acid chloride, β-chloroacryloyl chloride, benzoyl chloride, m-chlorobenzoyl chloride, p-toluyl chloride, p-methoxybenzoyl chloride, thiophene-2-carboxylic acid chloride, p-toluenesulphochloride and phenacetyl chloride.

EXAMPLE 20

16.5 parts of the compound of the formula (117) in 200 parts of anhydrous chlorobenzene are treated with 7 parts of dimethyl sulphate at 70° whilst stirring. The mixture is heated to 80°–85° for 5 hours, whereupon (117) dissolves and a yellow crystalline precipitate separates out. After cooling, this is filtered off, washed with toluene and dried in vacuo at 70°. 22 parts of the compound of the formula (132) 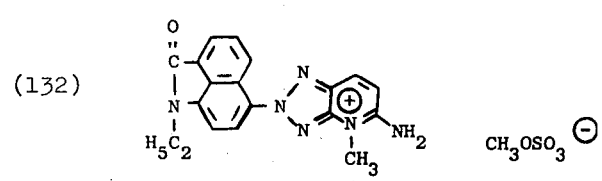

are obtained. This dissolves in water, alcohol or dimethylformamide to give a yellow colour and green-yellow fluorescence. In alcohol or dimethylformamide, the fluorescence is stronger than in water.

Analogous compounds are obtained if instead of compound (117) equivalent amounts of one of the remaining compounds indicated in Example 18 are employed. Analogous compounds are also obtained if instead of dimethyl sulphate an equivalent amount of one of the quaternising agents indicated in the table below are employed:

Table

| Quaternising agent | Reaction temperature | Compound No. | Colour of solution | Colour of fluorescence in DMF |
|---|---|---|---|---|
| Diethyl sulphate | 85° | (133) | yellow | green-yellow |
| p-Toluenesulphonic acid methyl ester | 110° | (134) | " | " |
| Benzyl chloride | 120–130° | (135) | " | " |
| Ethylene oxide in glacial acetic acid | 20–30° | (136) | " | " |
| Propylene oxide in glacial acetic acid | 20–30° | (137) | " | " |
| n-Butyl bromide | 140° (autoclave) | (138) | " | " |
| Allyl bromide | 130° (autoclave) | (139) | " | " |

The following compounds are manufactured analogously using the appropriate starting compounds: Table Compounds of the formula

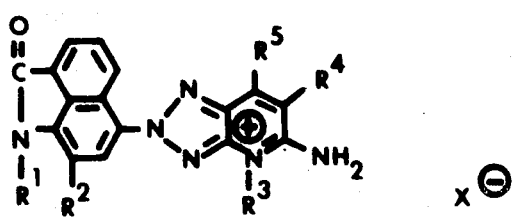

| Compound No. | R¹ | R² | R³ | R⁴ | R⁵ | X | Colour of solution | Colour of fluorescence in DMF |
|---|---|---|---|---|---|---|---|---|
| 140 | H | H | CH₃ | H | H | CH₃OSO₃⁻ | yellow | green-yellow |
| 141 | NC—CH₂—CH₂— | C₂H₅ | C₂H₅ | H | H | C₂H₅OSO₃⁻ | " | " |
| 142 | ⟨⟩—CH₂ | CH₃O | ⟨⟩—CH₂ | H | H | Cl⁻ | " | " |
| 143 | ⟨⟩— | H | CH₃O—CH₂—CH₂— | H | H | Br⁻ | " | " |
| 144 | CH₃(CH₂)₃— | H | HOOC—CH₂—CH₂ | H | H | Cl⁻ | " | " |
| 145 | CH₃ | Br | C₂H₅OCO—CH₂—CH₂ | H | H | CH₃COO⁻ | " | " |
| 146 | (CH₃)₂CH | Cl | CH₃O—⟨⟩—CH₂ | H | COOC₂H₅ | Cl⁻ | " | " |
| 147 | HO—CH₂—CH₂— | H | HO—CH₂—CH₂— | Br | H | CH₃COO⁻ | " | " |
| 148 | R¹ + R² = | CH₂—CH₂—CH₂ | CH₃—(CH₂)₃— | H | H | Br⁻ | " | " |
| 149 | ⟨H⟩—CH₂ | H | CH₃ | H | H | Cl⁻ | " | " |
| 150 | ⟨H⟩— | H | Cl—⟨⟩—CH₂ | H | Br | Cl⁻ | " | " |

EXAMPLE 21

3.7 parts of the comound of the formula (105) are suspended in 25 parts by volume of glacial acetic acid. 1.6 parts by volume of 98% strength nitric acid are added dropwise at 5°–10° whilst cooling and stirring. The mixture is stirred for a further 3 hours at 20° and the crystalline precipitate is filtered off at room temperature, washed with water until neutral and dried at 50° in vacuo. 4.5 parts of the compound of the formula (151) 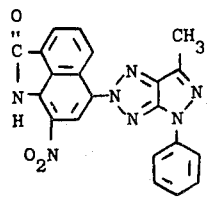

are obtained. The compound is purified by recrystallisation from 90 parts by volume of dimethylformamide. The substance dissolves in dimethylformamide to give a yellow colour and weak green-yellow fluorescence.

The reduction to the amino compound is carried out in dioxane with Raney nickel at 40° and 40 atmospheres gauge H₂ pressure. In this way, the compound of the formula (152) 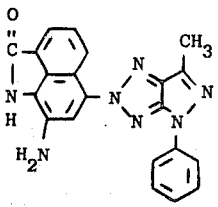

is obtained which dissolves in dimethylformamide to give a yellow colour and shows a strong green-yellow fluorescence.

If instead of compound (105) an equivalent amount of compound (52) is employed 3.0 parts of the compound of the formula (153) 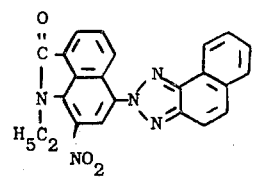

are obtained analogously after recrystallisation from 90 parts by volume of dimethylformamide. Reduction of (153) in dioxane with Raney nickel at 40°/40 atmospheres gauge H₂ yields the compound of the formula (154) 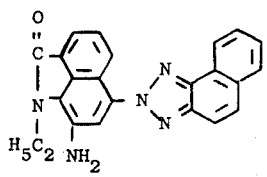

This dissolves in DMF to give a reddish-tinged yellow colour and reddish-tinged yellow fluorescence.

If instead of compound (105) an equivalent amount of compound (16) and (118) is employed, nitro compounds and amino compounds with similar valuable dyestuff properties to (151) – (154) are obtained analogously.

Warming (154) with acetic anhydride yields the corresponding acetylamino compound.

EXAMPLE 22

An approximately 1% strength dyeing with dyestuff (11) on polyethylene terephthalate fabric was produced as follows:

The fabric is introduced, at 50° and using a liquor ratio of 1:40, into a dye bath which contains the finely divided dyestuff, 2 g/l of a conventional anionic dispersing agent, 5 g/l of o-cresotic acid methyl ester and 1 g/l of $NaH_2PO_4$ and is adjusted to pH 4.5 – 5 with acetic acid. The temperature is raised to 80° – 85° over the course of 15 – 20 minutes and the bath is left in this temperature range for a further 20 minutes. Thereafter the liquor is gradually brought to the boil. After a boiling time of 1 – 1½ hours, the dyeing process is complete.

After rinsing and drying, brilliant very strongly greenish-tinged yellow dyeings having excellent fastness properties are obtained.

Brilliant, greenish-tinged dyeings are also obtained if instead of compound (11) one of the following dyestuffs is employed: (1) to (10), (12) to (25), (32) to (42), (44), (47), (52) to (54), (59), (93) to (99), (101 to (115) and (117) to (131).

EXAMPLE 23

An approximately 1.3% strength dyeing with dyestuff (44) on polyamide-6 fabrics was produced as follows:

The fabric is introduced at 40° and using a liquor ratio of 1:40 to 1:30, into a dye bath which contains 1 g/l of a conventional anionic dispersing agent and the finely divided dyestuff. The liquor temperature is raised to 98° (boiling point) over the course of 40 – 60 minutes and the bath is left at this temperature for about 60 minutes longer. Thereafter the fabric is rinsed and dried.

Greenish-tinged yellow dyeings with good fastness properties are obtained.

EXAMPLE 24

Polyethylene terephthalate fabric is impregnated on a padder at 40° with an aqueous liquor which contains, per liter, 10 g of finely disperse dyestuff of the formula (35), 7.5 g of sodium alginate, 20 g of triethanolamine and 20 g of octyl-phenyl-polyglycol-ether. The fabric is squeezed to a liquor content of about 100% and is dried at 100° and subsequently fixed for 30 seconds at 200° – 210°. After rinsing and drying, a brilliant, greenish-tinged yellow dyeing having very good fastness properties is obtained.

EXAMPLE 25

A fabric of polyethylene terephthalate is impregnated at room temerature with a clear padding liquor which contains 5.5 parts of dyestuff of the formula (36) in 994.5 parts of tetrachloroethylene. After squeezing out to a weight increase of 60%, the fabric is dried for one minute at 80°. Thereafter the dyestuff is fixed for 45 seconds at 220°. The fabric is washed for 20 seconds in cold tetrachloroethylene.

After drying, a brilliant, greenish-tinged yellow dyeing having very good fastness properties is obtained.

EXAMPLE 26

30 parts by weight of the disperse dyestuff of Example 21 are dissolved in a mixture of 50 parts by weight of thiodiglycol, 20 parts by weight of printing oil and 160 parts by volume of water. The solution is diluted with 200 parts of water and thickened with 400 parts of crystal gum, and a printable paste is produced by adding a further 60 to 100 parts of water. Polyethylene terephthalate fabrics are printed with this paste in the usual manner and are subsequently steamed for 20 minutes in a steamer at 103° – 105°. After soaping, rinsing with water and drying, a brilliant greenish-tinged yellow colour print is obtained, which is distinguished by good fastness to washing, rubbing, light and sublimation.

EXAMPLE 27

1.5 parts of dyestuff of the formula (27) are dissolved in 300 parts of hot water, 50 parts by volume of 10% strength ammonium acetate solution are added and the mixture is diluted with water to a liquor weight of 5,000 parts. Thereafter, 100 parts of poly-ε-caprolactam fabric are introduced into the dye bath at 50°, and the bath is heated to 100° over the course of 15 minutes. The dye bath is kept at this temperature for 1 hour but after 30 minutes 3 g of acetic acid are added. After rinsing and drying, a brilliant, greenish-tinged yellow dyeing having very good fastness properties is obtained.

Dyeings of similarly high brilliance and fastness are obtained if instead of the dyestuff of the formula (27) one of the following dyestuffs is employed: (28) to (31), (43), (45), (55), (100) and (103).

EXAMPLE 28

1 part of dyestuff of the formula (27) is dissolved in 200 parts of hot water and the solution is diluted with water to a liquor weight of 5,000 parts. Thereafter 100 parts of wool fibres are introduced into the dye bath at 40°, 3 parts of acetic acid are added, the bath is heated to the boil over the course of 15 minutes and dyeing is carried out for 1 hour at the boil, with 2 parts of formic acid being added after 30 minutes. After rinsing and drying, a brilliant greenish-tinged yellow dyeing having good fastness properties is obtained.

EXAMPLE 29

Polyacrylonitrile fibres are introduced, using a liquor ratio of 1:40, into an aqueous bath at 40°, which contains, per liter, 0.75 g of 30% strength acetic acid, 0.38 g of sodium acetate and 0.1 g of the dyestuff of the formula (132). The dye bath is heated to the boil over the course of 30 minutes and is kept at this temperature for 45 minutes. After rinsing and drying, a greenish-tinged yellow dyeing of high brilliance and excellent fastness properties is obtained.

Dyeings of a similarly high quality are obtained if instead of the dyestuff of the formula (132) one of the other dyestuffs listed in Example 20 is employed.

EXAMPLE 30

A polyacrylonitrile fabric is printed with a printing paste which has been manufactured in the following manner: 30 parts of dyestuff of the formula (132), 50 parts of thiodiethylene glycol, 30 parts of cyclohexanol and 30 parts of 30% strength acetic acid are recovered with 330 parts of hot water and the resulting solution is added to 500 parts of crystal gum (as the thickener). Finally, 30 parts by weight of zinc nitrate solution are also added.

The resulting print is dried, steamed for 30 minutes and subsequently rinsed. A brilliant, greenish-tinged yellow print of excellent fastness properties is obtained.

EXAMPLE 31

Acid-modified polyethylene terephthalate fibres are introduced, using a liquor ratio of 1:40, into an aqueous bath at 20° which contains, per liter, 5 g of sodium sulphate, 1 g of oleyl polyglycol ether (50 mols of ethylene oxide) and 0.15 g of the dyestuff of the formula (132) and which has been adjusted to pH 4 – 5 with acetic acid. The dye bath is heated to the boil over the course of 30 minutes and kept at the boil for 60 minutes. Thereafter the fibres are rinsed and dried. A brilliant, yellow dyeing having very good fastness properties is obtained.

EXAMPLE 32

Acid-modified synthetic polyamide fibres are introduced, using a liquor ratio of 1:40, into an aqueous bath at 40° which contains, per liter, 10 g of sodium acetate, 1 to 5 g of oleyl polyglycol ether (50 mols of ethylene oxide) and 0.15 g of the dyestuff of the formula (132) and has been adjusted to pH 4 – 5 with acetic acid. The dye bath is heated to the boil over the course of 30 minutes and is kept at the boil for 60 minutes. Thereafter the fibres are rinsed and dried. A brilliant, greenish-tinged yellow dyeing with good fastness properties is obtained.

EXAMPLE 33

Polyacrylonitrile fibres are introduced, using a liquor ratio of 1:10, into a perchloroethylene bath which contains, per liter, 1 g of oleic acid ethanolamide, 1 g of the reaction product of 1 mol of oleyl alcohol with 20 mols of ethylene oxide, 8 g of water, 1 g of glacial acetic acid and 1 g of the dyestuff of the formula (132). The dye bath is heated to 100° for 60 minutes with the dyeing apparatus closed and the liquor being agitated vigorously. Thereafter, the fibres are rinsed in perchloroethylene and dried in a stream of air. A very clear, greenish-tinged yellow dyeing having very good fastness properties is obtained.

EXAMPLE 34

A stock solution is prepared from 15 parts by weight of dyestuff of the formula (132), 15 parts by weight of polyacrylonitrile and 70 parts by weight of dimethylformamide, and this solution is added to a customary polyacrylonitrile spinning solution, the mixture being spun in a known manner. A clear, greenish-tinged yellow dyeing having good fastness properties is obtained.

EXAMPLE 35

0.3 part of the compound (38) are mixed with 100 parts of polystyrene. The mixture is kneaded at 180° – 200°C in an extruder to give a homogeneously coloured mass. This is extruded through a perforated plate. The resulting coloured polystyrene ribbons are cooled and then granulated in a beater mill (particle diameter about 2 – 4mm). The granules thus obtained are converted into mouldings in an injection moulding machine at 220° – 300°. Transparent, fluorescent mouldings are obtained, the colourations of which have very good light fastness and migration resistance.

EXAMPLE 36

100 parts by weight of unplasticised polyvinyl chloride, in the form of a suspension polymer, are plastically softened on a two-roll mixing mill at a roll temperature of 170°C and using a friction of 1:1.2. Thereafter, 0.5 part by weight of titanium dioxide and 0.8 part by weight of the compound (35) are added, the mixture is milled for 10 minutes, the polyvinyl chloride mass is charged onto a calender which can be heated, and 1 mm thick sheets are drawn off at 170°C. Yellow-coloured sheets of excellent fastness to migration and to light are obtained.

Instead of the compound (35), the compound (1) to (14), (16) to (20), (36) to (42), (93) to (98) and (118) to (130) can be employed with equal success.

EXAMPLE 37

Commercially available polymethacrylate granules are mixed dry with 0.5 per cent by weight of the compound (36) and the mixture is injection-moulded on a screw injection moulding machine at 220°C. The transparent mouldings which are coloured luminous yellow and have a strong yellow-green fluorescence possess very good fastness.

EXAMPLE 38

0.9 part of the compound (11) is mixed with 100 parts of finely divided polypropylene. The mixture is kneaded in an extruder at 210° to give a homogeneously coloured mass which is extruded at 280°–300° through a spinneret plate. Fibres with a strong green-yellow fluorescence are obtained, the colouration of which is transparent, rub-resistant and very fast to light.

We claim:

1. Naphtholactam dyestuff of the formula

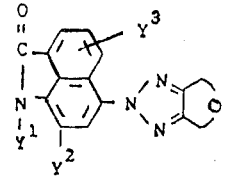

wherein
Y$^1$ is hydrogen, C$_1$-C$_5$-alkyl, benzyl, C$_1$-C$_2$-alkyl-benzyl, chlorobenzyl, C$_1$-C$_2$-alkoxybenzyl, cyanobenzyl, phenyl, C$_1$-C$_2$-alkylphenyl, chlorophenyl, C$_1$-C$_2$-alkoxyphenyl, cyclohexyl, or C$_1$-C$_5$-alkyl substituted by chloro, hyroxy, cyano, carboxy, carboxylic acid (C$_1$-C$_4$-alkyl) ester, benzyl ester, carboxylic acid amide, or C$_1$-C$_3$-alkoxy), Y$^2$ is hydrogen, chloro, bromo, C$_1$-C$_3$-alkyl, C$_1$-C$_2$-alkoxy, amino, or sulpho;

Y$^1$ and Y$^2$, when taken together, are propylene;

Y$^3$ is hydrogen or C$_1$-C$_2$-alkoxy; and

D is the remaining portion of a benzene ring which is unsubstituted or substituted by C$_1$-C$_4$-alkyl, C$_1$-C$_{12}$-alkoxy, amino, C$_1$-C$_4$-alkylamino, di(C$_1$-C$_4$-alkyl) amino, C$_1$-C$_6$-alkyl carbonylamino, C$_1$-C$_6$-alkylsulphonylamino, C$_1$-C$_6$-alkylcarbonyl (C$_1$-C$_3$-alkyl) amino, C$_1$-C$_6$-alkylsulphonyl (C$_1$-C$_3$-alkyl) amino, phenyl (C$_1$-C$_3$-alkyl) carbonylamino, phenyl (C$_1$-C$_3$-alkyl) sulphonylamino, halophenyl (C$_1$-C$_3$-alkyl) carbonylamino, halophenyl (C$_1$-C$_3$-alkyl) carbonyl (C$_1$-C$_3$-alkyl) amino, benzoylamino, phenylsulphonylamino, substituted phenylsulphonylamino wherein the substituent is halo, C$_1$-C$_4$-alkyl, C$_1$-C$_4$-alkoxy, cyano, or carboxylic acid C$_1$-C$_4$-alkyl ester;

in addition D is the remaining portion of a pyridine ring or the quaternary salt thereof wherein said ring is unsubstituted or substituted by bromo, methyl, carbomethoxy, amino, amino substituted by acetyl, trifluoroacetyl, chloropropionyl, chloroethylsulphonyl, 2,2,3,3-tetrafluorocyclobutyl-1-carbonyl, chloroacryloyl, benzoyl, chlorobenzoyl, toluyl, methoxybenzoyl, toluenesulphonyl, or phenacetyl; and wherein halo is chloro or bromo.

2. Naphtholactam dyestuff of the formula

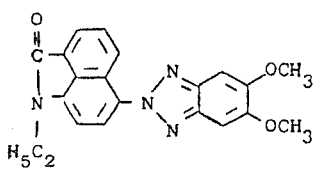

3. Naphtholactam dyestuff of the formula

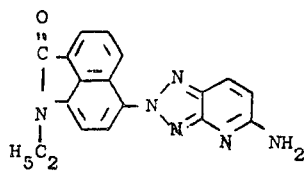

4. Naphtholactam dyestuff of the formula

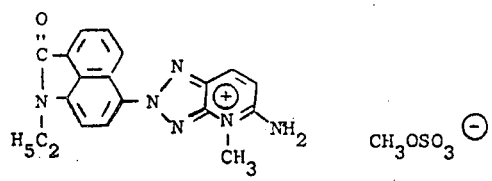

5. Naphtholactam dyestuff of the formula

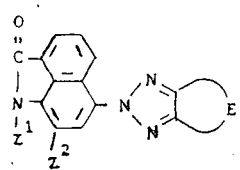

wherein
- $Z^1$ is hydrogen, benzyl, $C_1$-$C_4$-alkyl, or $C_1$-$C_4$-alkyl substituted by hydroxy, chloro, or cyano;
- $Z^2$ is hydrogen, methyl, ethyl, or amino; and
- E is the remaining portion of a benzene ring which is unsubstituted or substituted by $C_1$-$C_2$-alkyl, $C_1$-$C_4$-alkoxy, amino, $C_1$-$C_4$-alkylamino, di($C_1$-$C_4$-alkylcarbonylamino, $C_1$-$C_4$-alkylsulphonylamino, $C_1$-$C_4$-alkylcarbonyl ($C_1$-$C_2$-alkyl) amino, $C_1$-$C_4$-alkylsulphonyl ($C_1$-$C_2$-alkyl) amino, phenylacetylamino, benzylsulphonylamino, benzoylamino, or phenylsulphor amino.

6. Naphtholactam dyestuff of the formula

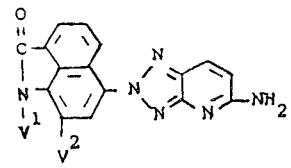

or the corresponding quaternary salt of the formula

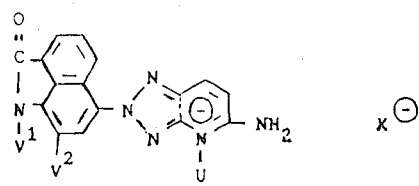

wherein
- $V^1$ is hydrogen, benzyl, $C_1$-$C_4$-alkyl, or $C_1$-$C_4$-alkyl substituted by hydroxy, chloro, or cyano;
- $V^2$ is hydrogen, methyl, ethyl, or amino; and
- U is benzyl, chlorobenzyl, methoxybenzyl, $C_1$-$C_4$-alkyl, or $C_1$-$C_4$-alkyl substituted by $C_1$-$C_2$-alkoxy, hydroxy, cyano, carboxy, or carboxylic acid $C_1$-$C_2$-alkyl ester; and
- X is an anion.

7. Dyestuff of claim 6 wherein $V^1$ is methyl, β-hydroxyethyl, β-cyanoethyl, β-hydroxypropyl, benzyl, butyl, isopropyl; and
$V^2$ is hydrogen or ethyl.

8. Naphtholactam dyestuff of claim 5 of the formula

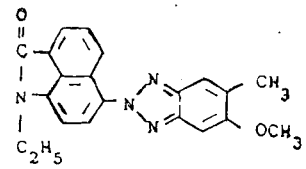

* * * * *